US010434440B2

United States Patent
Shreve

(10) Patent No.: US 10,434,440 B2
(45) Date of Patent: Oct. 8, 2019

(54) MOBILE PHASE CONTROLLER FOR SUPERCRITICAL FLUID CHROMATOGRAPHY SYSTEMS

(71) Applicant: Waters Technologies Corporation, Milford, MA (US)

(72) Inventor: Joshua A. Shreve, Franklin, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 530 days.

(21) Appl. No.: 14/911,046

(22) PCT Filed: Aug. 8, 2014

(86) PCT No.: PCT/US2014/050353
§ 371 (c)(1),
(2) Date: Feb. 9, 2016

(87) PCT Pub. No.: WO2015/023533
PCT Pub. Date: Feb. 19, 2015

(65) Prior Publication Data
US 2016/0199751 A1 Jul. 14, 2016

Related U.S. Application Data

(60) Provisional application No. 61/864,856, filed on Aug. 12, 2013.

(51) Int. Cl.
*B01D 15/16* (2006.01)
*B01D 15/40* (2006.01)
(Continued)

(52) U.S. Cl.
CPC ............ *B01D 15/40* (2013.01); *B01D 15/16* (2013.01); *B01D 15/163* (2013.01); *G01N 30/02* (2013.01);
(Continued)

(58) Field of Classification Search
CPC ...... B01D 15/40; B01D 15/16; B01D 15/163; B01D 15/18; G01N 30/32; G01N 30/34;
(Continued)

(56) References Cited

U.S. PATENT DOCUMENTS 4,982,597 A    1/1991  Berger
4,984,602 A    1/1991  Saito et al.
(Continued)

FOREIGN PATENT DOCUMENTS

EP              0309380 A2       3/1989
WO         WO-2013167193 A1 *  11/2013   ........... G01N 30/463
WO           2014/201222 A1    12/2014

OTHER PUBLICATIONS

Supplementary European Search Report for European Patent Application No. 14835931.8; dated Mar. 1, 2017.
(Continued)

*Primary Examiner* — Benjamin L Lebron
(74) *Attorney, Agent, or Firm* — Womble Bond Dickinson (US) LLP; Deborah M. Vernon; Heath T. Misley

(57) ABSTRACT

The present disclosure relates to an apparatus for regulating the average mobile phase density or pressure in a carbon dioxide based separation system. The apparatus includes a controller, a set of pressure or density sensors and a set of instructions capable of determining the pressure drop across a column and adjusting at least one system component or parameter to achieve a pre-determined average mobile phase density or pressure in the system.

17 Claims, 19 Drawing Sheets

(51) Int. Cl.
*G01N 30/02* (2006.01)
*G01N 30/32* (2006.01)
*G01N 30/34* (2006.01)
*G01N 30/46* (2006.01)

(52) U.S. Cl.
CPC .............. *G01N 30/32* (2013.01); *G01N 30/34* (2013.01); *G01N 30/46* (2013.01)

(58) Field of Classification Search
CPC .... G01N 30/463; G01N 30/465; G01N 30/72; G01N 30/6095; G01N 2030/326; G01N 2030/322; G01N 2030/328; G01N 27/44704; G01N 30/02; G01N 30/46; F04B 11/0075; F04B 23/06
See application file for complete search history.

(56) References Cited

U.S. PATENT DOCUMENTS

| | | | |
|---|---|---|---|
| 5,305,232 A | | 4/1994 | Chimowitz et al. |
| 5,476,000 A | | 12/1995 | Henderson et al. |
| 2003/0165628 A1* | | 9/2003 | Simmons ................ B05B 9/005 427/345 |
| 2008/0166817 A1* | | 7/2008 | Gillespie .............. G01N 30/468 436/161 |
| 2009/0275119 A1 | | 11/2009 | Sugiyama et al. |
| 2010/0040483 A1 | | 2/2010 | Berger et al. |
| 2010/0102008 A1 | | 4/2010 | Hedberg |
| 2011/0306146 A1 | | 12/2011 | Sidhu et al. |
| 2012/0285872 A1 | | 11/2012 | Shreve et al. |
| 2013/0048095 A1 | | 2/2013 | Wikfors et al. |

OTHER PUBLICATIONS

International Search Report for PCT/US2014/050353; International Filing Date Aug. 8, 2014.
HPLC Separation Fundamentals. Agilent Technologies. Accessed on Jan. 9, 2018 from https://www.agilent.com/cs/library/eseminars/Public/HPLc')/020Separation°/020Fundamentals_020811.pdf. Publication date Feb. 8, 2011.
International Preliminary Report on Patentability of the International Bureau of WIPO and Written Opinion of the International Searching Authority, dated Dec. 15, 2015.
International Search Report of the International Searching Authority for PCT/US2014/042076, dated Oct. 7, 2014.

* cited by examiner

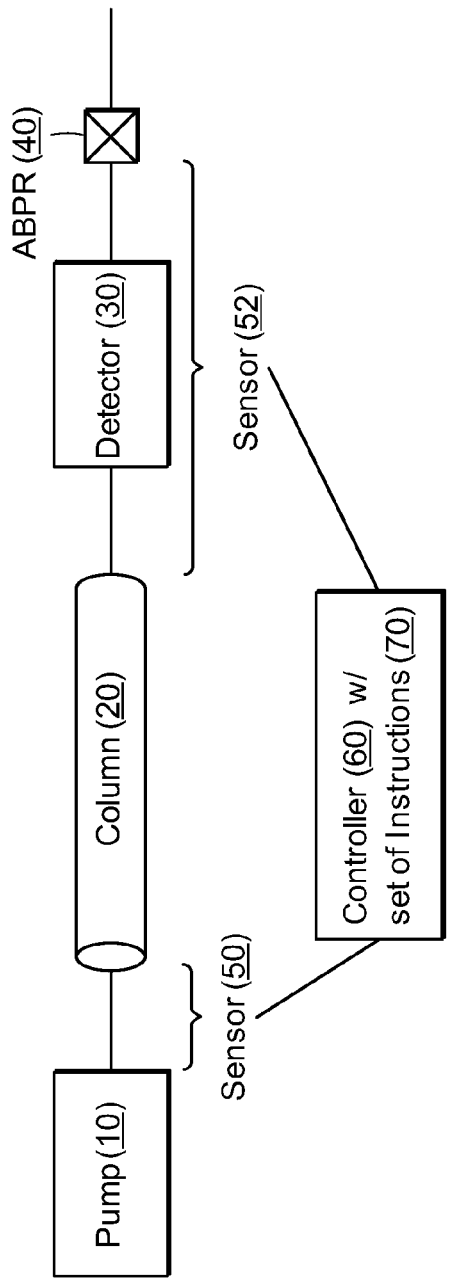
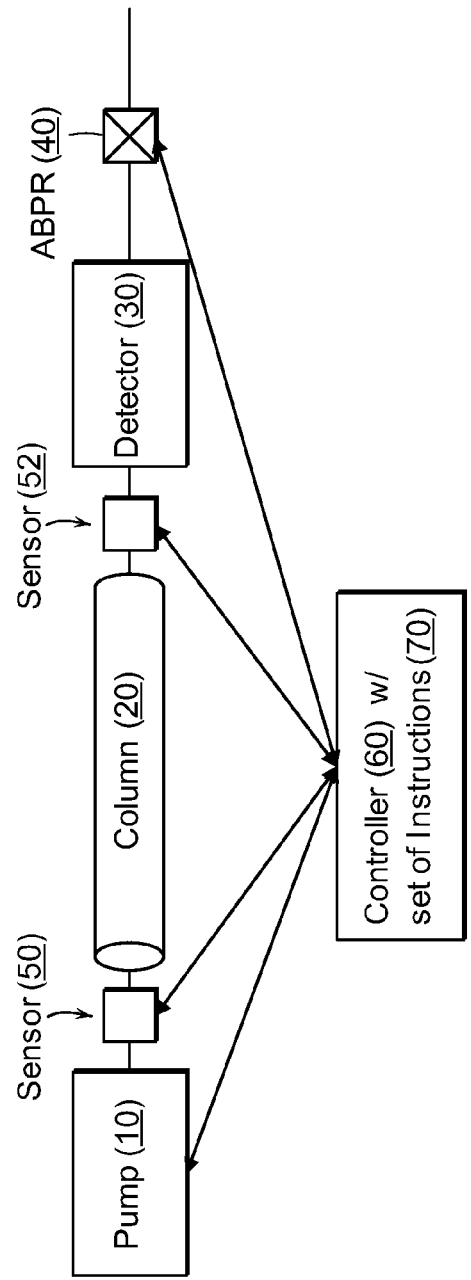
FIG. 1A
FIG. 1B

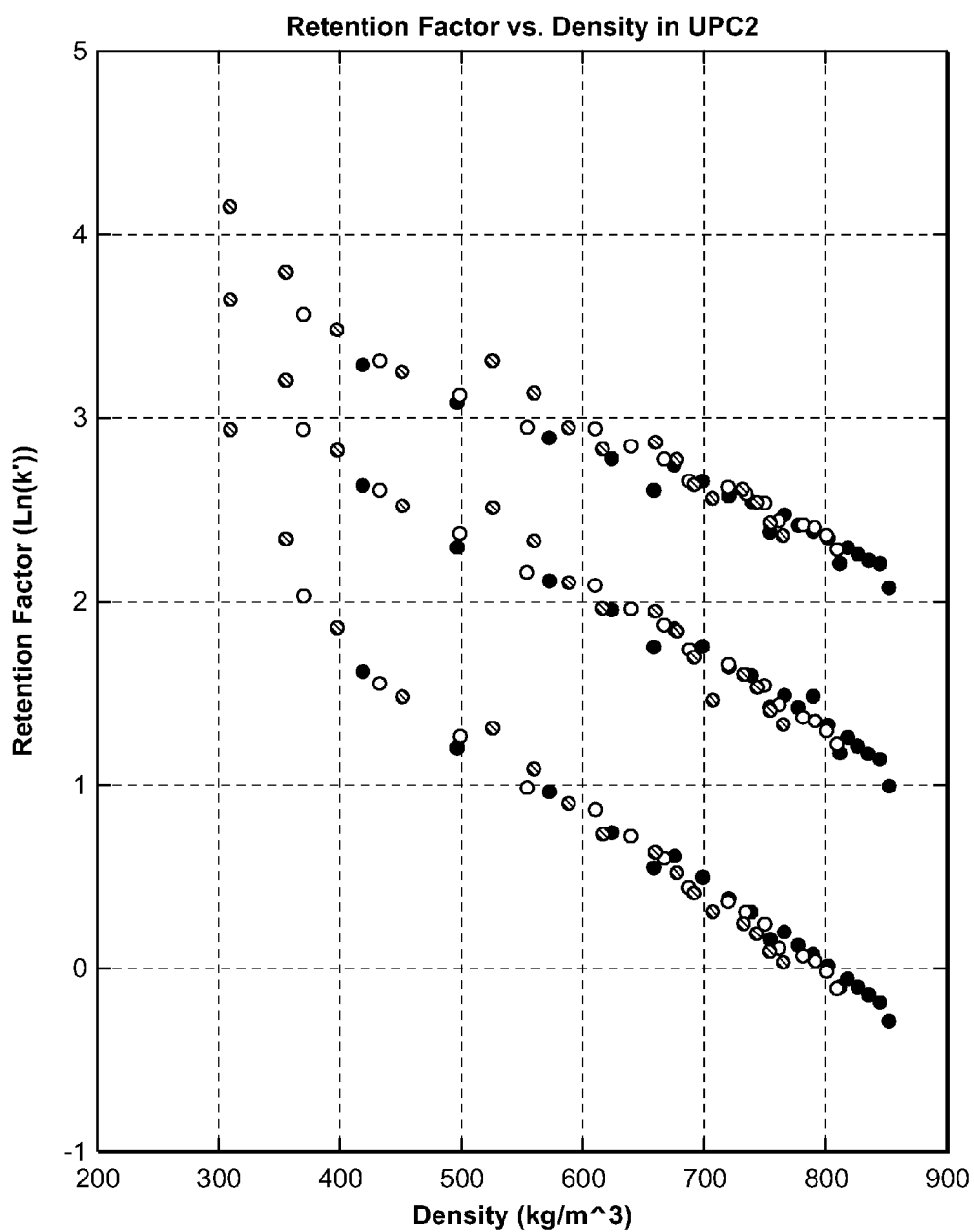

MOBILE PHASE CONTROLLER FOR SUPERCRITICAL FLUID CHROMATOGRAPHY SYSTEMS

CROSS-REFERENCE TO RELATED APPLICATIONS

This application is a National Stage Application of International Application Number PCT/US2014/050353, filed Aug. 8, 2014, which claims priority to U.S. Provisional Application No. 61/864,856, filed Aug. 12, 2013. Each of the foregoing applications are incorporated herein by reference in their entirety.

FIELD OF THE TECHNOLOGY

The present disclosure relates to an apparatus for controlling the average mobile phase density or pressure in a supercritical fluid chromatography system and/or a carbon dioxide based chromatography system. The apparatus, and related methodology, involves mobile phase density or pressure regulation to approximate or maintain average solvent properties in the region of interest in the chromatographic system.

BACKGROUND

Developing a successful chromatographic separation usually requires extensive method development. Such method development often involves the evaluation and optimization of numerous variables. These variables may include the choice of chromatographic system, e.g., carbon dioxide based chromatography, SFC, HPLC, GC, the choice of mobile phase, the choice of column chemistry and column dimensions, the choice of detector, etc. Once a successful chromatographic separation has been developed it will invariably need to be transferred and performed on different chromatographic systems. For example, an analytical scale SFC separation may need to be transferred and performed on a preparative scale SFC system.

For liquid chromatography, the theory and understanding for transferring methods between different system or column configurations is generally well understood. Guidelines for transferring LC methods are straightforward. Method transfers under LC conditions typically do not need additional optimization. In SFC and/or carbon dioxide based chromatography, however, there is currently no such apparatus or methodology in place to facilitate method transfer. Chromatographic separations using carbon dioxide as a mobile phase that are transferred from one chromatographic system to another chromatographic system typically need to be re-developed to achieve the same successful separation as achieved on the original chromatographic system. Re-development is time-consuming, expensive and wasteful.

SUMMARY

The present disclosure relates to an apparatus, and related methodology, for controlling mobile phase density or pressure in a supercritical fluid chromatography system and/or a carbon dioxide based chromatography system.

In one embodiment, the present disclosure relates to an apparatus for regulating the average mobile phase density or pressure in a carbon dioxide based separation system having a controller; a first sensor and a second sensor both in signal communication with the controller, and a set of instructions utilized by the controller. The first sensor is capable of measuring a first mobile phase density or pressure in the system and the second sensor is capable of measuring a second mobile phase density or pressure in the system. The controller is capable of averaging the first and the second mobile phase density or pressure measurements to determine an average mobile phase density or pressure value and adjusting at least one system component or parameter to achieve a pre-determined average mobile phase density or pressure in the system in response to the average mobile phase density or pressure value.

In another embodiment, the present disclosure relates to a carbon dioxide based separation system having a pump, a column located downstream of the pump, at least one back pressure regulator located downstream of the column, a first sensor located upstream of the column, a second sensor located downstream of the column, a controller in signal communication with the first and second sensors, and a set of instructions utilized by the controller. The first sensor is capable of measuring a first mobile phase density or pressure in the system and the second sensor is capable of measuring a second mobile phase density or pressure in the system. The controller is capable of averaging the first and the second mobile phase density or pressure measurements to determine an average mobile phase density or pressure value and adjusting at least one system component or parameter to achieve a pre-determined average mobile phase density or pressure in the system in response to the average mobile phase density or pressure value.

In another embodiment, the present disclosure relates to a method of achieving a pre-determined average mobile phase density or pressure in a carbon dioxide based separation system described above, involving determining an average mobile phase density or pressure in the system, comparing the average mobile phase density or pressure with the pre-determined average mobile phase density or pressure, and adjusting at least one system component or parameter to achieve the pre-determined average mobile phase density or pressure.

In the embodiments of the present disclosure, the sensors may be density sensors for measuring mobile phase density in the system or pressure sensors for measuring mobile phase pressure in the system. The first sensor may be contained in or connected to the pump, may be contained in or connected to the head of the column, or positioned anywhere in between. The second sensor may be contained in or connected to the back pressure regulator, may be contained in or connected to the end of the column, or positioned anywhere in between. In some embodiments, the mobile phase density or pressure in the system may be at equilibrium when the first and second mobile phase density or pressure measurements are measured by the first and second sensors, or when the at least one system component or parameter is adjusted. In other embodiments, the mobile phase density or pressure in the system is not at equilibrium when the first and second mobile phase density or pressure measurements are measured by the first and second sensors, or when the at least one system component or parameter is adjusted.

The apparatus and methodology of the present disclosure allows for the control of mobile phase density or pressure in a supercritical fluid chromatography system and/or a carbon dioxide based chromatography system. The apparatus and methodology also allows for the efficient transfer of carbon dioxide based chromatographic methods between different system and/or column configurations. Using the apparatus and methodology of the present disclosure, the same successful separation on one system can be transferred to a second system without excessive time, money or resources being expended on re-optimizing the second separation on the second system. The apparatus and methodology facilitates the transfer of methods between different systems that have different pressure profiles, e.g. carbon dioxide based chromatographic systems having different columns configurations and/or operating conditions, e.g. different column temperatures.

BRIEF DESCRIPTION OF THE DRAWINGS

The foregoing and other features and advantages provided by the present disclosure will be more fully understood from the following description of exemplary embodiments when read together with the accompanying drawings.

FIG. 1 shows two embodiments (1A and 1B) of a separation system and exemplary locations where the mobile phase density or pressure sensors, e.g., transducers, and controller may be located and the density and pressure values may be determined.

FIGS. 15A, 15B, 16A and 16B show the effect on retention time (FIGS. 15A and 15B) and selectivity (FIGS. 16A and 16B) of changing density for a number of analytes.

DETAILED DESCRIPTION

Figure 2A:
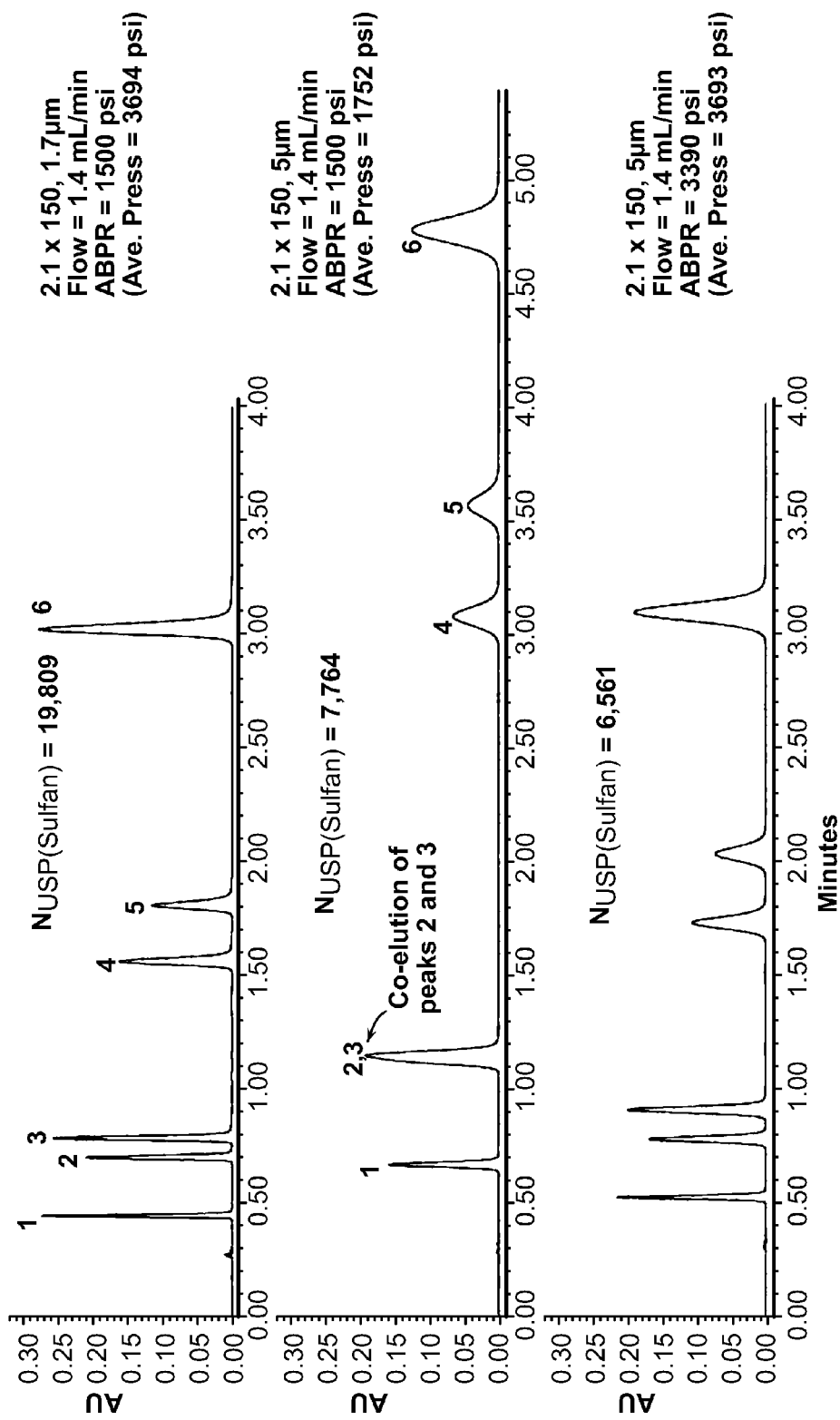
FIG. 2a demonstrates the transfer of a method developed on a 1.7 μm particle to a larger 5 μm particle, with and without matching the average density or average pressure profile for the separation. For this separation, the flow rate was not scaled to the optimum linear velocity.

Analyte retention factors in carbon dioxide based chromatographic separations are influenced by the mobile phase density. The mobile phase density can change significantly with changes in pressure under isothermal conditions, which is one of the reasons why its density varies over a wide range during pumping events, especially if combined with a relatively incompressible fluid, such as a modifier downstream of the pump. Carbon dioxide is highly compressible under standard operating conditions. Typically, retention factors decrease as mobile phase density (or pressure) increases.

Some analytes, however, may respond differently to changes in mobile phase density as a result of changes in system configuration. For example, the selectivity and resolution of target analytes may be disproportionately impacted as each responds differently to the same changes in system conditions, e.g., mobile phase density or system pressure. This differential response can present a challenge to optimizing the consistency of a separation or when attempting to transfer methods between different carbon dioxide based chromatographic systems that involve changes in the mobile phase density or column pressure profiles for the separation.

For example, a change in column length or particle size can affect the overall system density and pressure profile. A common example is the scale up of an analytical scale separation developed using a sub-2 μm particle size stationary phase to a preparative scale separation using a 5 μm particle size stationary phase. The difference in the density and pressure profiles across the column, between the analytical and the preparative system, can lead to very different chromatography.

Without wishing to be bound by any particular theory, it is believed that by matching the mobile phase density profile that a particular target analyte experiences between two separation systems, using the same column chemistry, the analyte retention factors and separation efficiency may be maintained. Therefore, it would be advantageous to have a characterized mobile phase density profile for any separation. The average density profile could then be maintained during optimization of a separation or transfer of methods between different system and/or column configurations.

Equipment to measure mobile phase densities is expensive. The calculation of densities is difficult because of the often changing temperature, pressure, mobile phase composition and viscosities used for separations. As an approximation, the column pressure, e.g., system pressure measured at the pump and the backpressure regulator outlet pressure (ABPR), can be used to calculate the average column pressure for a separation. These pressure measurements are easier to obtain than density measurements. The maintenance of this average column pressure between separations is a close approximation to the maintenance of the average mobile phase density across the separation. Matching either the average mobile phase density or the average column pressure between two carbon dioxide based chromatographic separations can result in separations having target analytes with similar selectivity and retention factor characteristics.

In one embodiment, the present disclosure relates to an apparatus for regulating the average mobile phase density or pressure in a carbon dioxide based separation system having a controller, a first sensor and a second sensor both in signal communication with the controller, wherein the first sensor is capable of measuring a first mobile phase density or pressure in the system and the second sensor is capable of measuring a second mobile phase density or pressure in the system, and a set of instructions utilized by the controller, wherein the controller is capable of averaging the first and the second mobile phase density or pressure measurements to determine an average mobile phase density or pressure value and adjusting at least one system component or parameter to achieve a pre-determined average mobile phase density or pressure in the system in response to the average mobile phase density or pressure value.

The present disclosure also relates to efficiently transferring carbon dioxide based separations between systems. As provided herein, the phrase "efficiently transferring" of a carbon dioxide based separation refers to the concept of transferring a separation, methodology or method parameters between carbon dioxide based separation systems while maintaining the chromatographic integrity of the separation, e.g., preserving retention factors and selectivity of at least one target analyte, preferably two or more target analytes. An efficiently transferred separation is one that substantially reproduces the chromatographic integrity of the separation obtained on the first system on the second system. For example, an efficiently transferred separation is one wherein the second carbon dioxide based separation performed on the second system has a target analyte, or target analytes, having substantially the same retention factor (k') or selectivity as the first carbon dioxide based separation performed on the first system.

As provided herein, the term "pre-determined average mobile phase pressure or density" refers to an average mobile phase pressure or density determined or calculated from a first separation system or simulation/approximation wherein the chromatographic integrity of the first separation or simulation/approximation is substantially maintained on the second separation system or subsequent separation system.

As provided herein, the term "retention factor" or "(k')" refers to the ratio of time an analyte is retained in the stationary phase to the time it is retained in the mobile phase under either isocratic or gradient conditions. For an efficiently transferred carbon dioxide based chromatographic method, the difference in retention factor for any given target analyte between a first and a second separation should be minimized. Preferably, the difference in retention factor for a target analyte between a first and a second separation is less than about 10%. More preferably, the difference in retention factor for a target analyte between a first and a second separation is less than about 5%. Even more preferably, the difference in retention factor for a target analyte between a first and a second separation is less than about 1%.

For multiple target analytes, the difference in retention factor for each target analyte, respectively, between a first and a second separation should also be minimized. Multiple target analytes may include 2 or more target analytes, e.g., 2, 3, 4, 5, 6, 7, 8, 9, 10, etc. Preferably, all or a majority of the target analytes have substantially the same retention factor between the first and second separations. Because all analytes respond differently to system changes, not all of the target analytes may have substantially the same retention factor between the first and second separations. Preferably, the difference in retention factor for each multiple target analyte, respectively, between a first and a second separation is less than about 10%. More preferably, the difference in retention factor for each multiple target analyte, respectively, between a first and a second separation is less than about 5%. Even more preferably, the difference in retention factors for each multiple target analyte, respectively, between a first and a second separation is less than about 1%.

As provided herein, the term "selectivity" or "selectivity factor" or "$\alpha$" refers to the degree of separation of two analytes in a separation. For example, the selectivity factor for two analytes, A and B, is the ratio of their respective retention factors, provided A elutes before B, e.g., $\alpha=k'_B/k'_A$.

The selectivity between two target analytes between a first and a second separation should be maintained. Preferably, the change in selectivity for two target analytes between a first and a second separation is less than about 10%. More preferably, the change in selectivity for two target analytes between a first and a second separation is less than about 5%. Even more preferably, the change in selectivity for two target analytes between a first and a second separation is less than about 1%.

As provided herein, the phrase "a carbon dioxide based separation procedure" refers to system requirements, method parameters and/or settings used with a particular carbon dioxide based separation system to control or effect a separation of target analytes on the particular carbon dioxide based separation system. The mobile phase in a carbon dioxide based separation or chromatography system includes at least, in part, carbon dioxide.

In some embodiments, the present disclosure relates to chromatography systems and chromatographic separations that use other mobile phase solvents or compositions that have similar compressibility properties as carbon dioxide at pumping temperatures and pressures, such as freon. Preferably, the other mobile phase solvents or compositions exhibit the same or similar effect on analyte behavior due to changes in mobile phase density or pressure as described herein.

As provided herein, the phrase "separation system" refers to instrumentality or equipment, e.g., a pump, a column, a detector and accompanying accessories, that are used to perform the separation and detection of target analytes. In some configurations, the separation system may exclude one or more of these components, e.g., pump or detector.

The distinction between different separation systems, e.g., a first separation system and a second separation system, may include any change in the system configuration that results in a change in the overall operating average mobile phase density or average column pressure. For example, the distinction between different separation systems may be the use of different instruments such as a carbon dioxide based analytical chromatography system, for example a system commercially available from Waters Technologies Corporation (Milford, Mass.) and branded as an ACQUITY® UPC$^2$ system versus a carbon dioxide based preparative chromatography system, for example a system commercially available from Waters Technologies Corporation (Milford, Mass.) and branded as a Prep 100 SFC system. The distinction may also be a change in one or more components on the same instrument, e.g., a change in system configuration. For example, the distinction may be a change in column configuration, e.g. length, internal diameter or particle size, or a change in tubing, e.g., length or internal diameter, or the presence of a tubing valve. The distinction may also be a change in a separation parameter or condition, such as flow rate or temperature. Preferably, the present disclosure may be applied to any change or distinction, e.g. instrument, column particle size, column length, flow rate, etc., between different separation systems which results in greater than about a 10% change in overall operating average mobile phase density or average column pressure. More preferably, the present disclosure may be applied to any change or distinction which results in greater than about a 5% change in overall operating average mobile phase density or average column pressure. Even more preferably, the present disclosure may be applied to any change or distinction which results in greater than about a 1% change in overall operating average mobile phase density or average column pressure.

Column stationary phases may differ in regard to chemistry, base particle, ligand, bonding density, endcapping, pore size, etc. Column manufacturers typically produce columns having the same stationary phase, e.g., same chemistry, same base particle, same ligand, same bonding density, same endcapping and same pore size, in several different particle size and column dimension configurations. In one embodiment, the two different separation systems have a first and a second respective column, wherein the first and second columns have similar stationary phases. The similar stationary phases may have, at least, same chemistry, same base particle, same ligand, same bonding density, same endcapping or same pore size. Preferably, the similar stationary phases have the same chemistry.

The present disclosure may be useful for transferring separations between analytical scale systems, preparative scale systems and combinations thereof. For example, the present disclosure may be useful in transferring a separation from an analytical scale system to a preparative scale system, or a preparative scale system to an analytical scale system. The present disclosure may also be useful in transferring a separation from one analytical scale system to another analytical scale system, or from one preparative scale system to another preparative scale system. A list of systems for which the present disclosure may be applicable include, but is not limited to, carbon dioxide based chromatography systems commercially available from Waters Technologies Corporation (Milford, Mass.) and branded as ACQUITY® UPC$^2$, Method Station SFC, Resolution SFC MS, Preparative SFC Instruments (e.g., Investigator SFC, Prep 100 SFC, SFC 80/200/350 Preparative Systems), UPC$^2$ and SFC columns including both chiral and achiral stationary phases.

In another embodiment, the present disclosure relates to a carbon dioxide based separation system having a pump, a column located downstream of the pump, at least one back pressure regulator located downstream of the column, a first sensor located upstream of the column, wherein the first sensor is capable of measuring a first mobile phase density or pressure in the system, a second sensor located downstream of the column, wherein the second sensor is capable of measuring a second mobile phase density or pressure in the system, a controller in signal communication with the first and second sensors; and a set of instructions utilized by the controller, wherein the controller is capable of averaging the first and the second mobile phase density or pressure measurements to determine an average mobile phase density or pressure value and adjusting at least one system component or parameter to achieve a pre-determined average mobile phase density or pressure in the system in response to the average mobile phase density or pressure value.

The present disclosure also relates to a method of achieving a pre-determined average mobile phase density or pressure in a carbon dioxide based separation system, including determining an average mobile phase density or pressure in the system; comparing the average mobile phase density or pressure with the pre-determined average mobile phase density or pressure; and adjusting at least one system component or parameter to achieve the pre-determined average mobile phase density or pressure. The average mobile phase density or pressure in the system may be determined by measuring a first mobile phase density or pressure at a first sensor and a second mobile phase density or pressure at a second sensor to generate a first set of measurements; and calculating the average mobile phase density or pressure from the first set of measurements. The method may also include transmitting the first set of measurements to the controller to calculate the average mobile phase density or pressure in the system.

In one embodiment, the present disclosure also relates to a method of achieving the pre-determined average mobile phase density or pressure in the carbon dioxide based separation system as described herein including measuring a first mobile phase density or pressure at the first sensor and a second mobile phase density or pressure at the second sensor to generate a first set of measurements, transmitting the first set of measurements to the controller, calculating the average mobile phase density or pressure from the first set of measurements, comparing the average mobile phase density or pressure from the first set of measurements with the pre-determined average mobile phase density or pressure, and adjusting at least one system component or parameter to achieve the pre-determined average mobile phase density or pressure. The first mobile phase density or pressure and the second mobile phase density or pressure may be measured simultaneously.

In one embodiment, the method further includes repeating one or more of the steps above, e.g. measuring through adjusting, until the pre-determined average mobile phase density or pressure is achieved. The mobile phase density or pressure in the system may not at equilibrium when the first and second mobile phase density or pressure measurements are measured by the first and second sensors and the adjustments are performed to the system, i.e., the system may be dynamically adjusted. The time between consecutive measurements and adjustments of the at least one system component or parameter is less than the time for the system density and/or pressure to equilibrate after the prior adjustment. Preferably, the time is less than about 10 seconds, more preferably less than about 5 seconds, and even more preferably less than about 1 second.

The present disclosure involves matching, or substantially matching, the average mobile phase density profile or average column pressure profile that a particular target analyte experiences between the two separation systems. In some embodiments, the disclosure involves matching, or substantially matching, the average mobile phase density profile or average column pressure profile that multiple target analytes experience between the two systems. In a carbon dioxide based separation system, the largest density and pressure change in the system is usually the density or pressure drop across the column. Determining the average mobile phase density, e.g., the average column mobile phase density, may be performed using density sensors upstream and downstream of the column. In some embodiments, other components may also cause a density or pressure drop across the component, e.g., some detectors located before the backpressure regulator, tubing, or tubing valve. The density or pressure drop across these components also contribute to the average mobile phase density. Density or pressure measurements may be taken upstream, downstream or across these other components.

In one embodiment, the first sensor is a first density sensor capable of measuring a first mobile phase density in the system and the second sensor is a second density sensor capable of measuring a second mobile phase density in the system. In another embodiment, the first sensor is a first pressure sensor capable of measuring a first mobile phase pressure in the system and the second sensor is a second pressure sensor capable of measuring a second mobile phase pressure in the system. For example, in a simple carbon dioxide based chromatographic system may have a pressure sensor to measure the system pressure at the pump, or the beginning of the system, and another sensor at the ABPR, or the end of the system, to approximate the average column pressure. The first pressure sensor (or density sensor) may be contained in or connected to the pump. The second pressure sensor (or density sensor) may be contained in or connected to the back pressure regulator. In this system, the majority of the system pressure drop occurs in the column. In a more complex system, additional system pressure drops may occur due to other components, e.g., a pressure drop due to the tubing valve. A more complex calculation can be preformed to account for these additional drops, such as by modification to vary the weighing factors of the pressure readings from the various sensors.

Additional pressure drop in the system which are not associated with the column may be addressed by a number of different strategies. In one embodiment, the simplest strategy is to perform a test to measure the non-column pressure drop at the method conditions and subtract the pre-column pressure drop from the pump pressure and add the post-column pressure drop to the ABPR pressure. This strategy provides an accurate value of the non-column pressure drop, but is time consuming and requires additional testing. In another embodiment, another strategy is to perform a test to generally characterize the system. The characterization can be entered into a basic model that estimates the drops for any given condition based on either a full complex model or a simplified version of the full model. The general characterization of the system can be performed by running the system with the column bypassed (e.g., can use a column select valve to bypass the column in the CM-A). The overall non-column pressure drop combined with the system information can provide accurate estimates of the necessary adjustments to the measured pressures. Finally, in another embodiment, a further strategy is to input the system configuration and use the known plumbing to calculate the pressure based on a full or simplified model including the method conditions. A set of standard configurations can be used and characterized that could be selected from in the method or the user could manually enter the data for each instrument.

FIG. 1 shows one embodiment of the present disclosure. The separation system includes a pump (10), a column (20) located downstream of the pump (10), a detector (30) located downstream of the column (20), an active back pressure regulator (40) located downstream of the detector (30). As shown in FIG. 1A, at any point between or at the pump (10) and the column (20) a first sensor (50) may be located. Also, at any point between or at the column (20) and the ABPR (40) a second sensor (52) may be located. As shown in FIG. 1B, the sensors (50, 52) are located between the pump (10) and the column (20), and the column (20) and the detector (30) (i.e., upstream of the ABPR), respectively. The sensors (50, 52) are connected to, and in signal or data communication with, the controller (60). The controller (60) contains or has inputted a set of instructions (70) that may be used to calculate new parameters or system settings or conditions. The controller (60) is also connected to, and in signal or data communication with the pump (10) and the ABPR (40). The controller (60) is capable of receiving data or signals over these connections and/or sending data or signals over these connections to all, or most, of the components it is connected to.

Preferably, the location(s) for measuring the density or pressure in a first system is similar or equivalent to the location(s) in a second system. For example, if the location for measuring the density or pressure upstream of the column for the first system is at the pump then preferably the location for measuring the density or pressure upstream of the column for the second system is also at the pump. If the location for measuring the density or pressure downstream of the column for the first system is at the backpressure regulator then preferably the location for measuring the density or pressure downstream of the column for the second system is also at the backpressure regulator.

In one embodiment, the average mobile phase density or average column pressure is the average mobile phase density or pressure calculated from (i) the inlet mobile phase density or pressure measured at the head of the column and (ii) the output mobile phase density or pressure measured at the base of the column. In another embodiment, the average mobile phase density or average column pressure is the average mobile phase density or pressure calculated from (i) the mobile phase density or pressure measured at the output of the pump and (ii) the mobile phase density or pressure measured at the ABPR inlet. Combinations of these embodiments may also be used to determine the average mobile phase density or average column pressure.

The present disclosure is applicable to both isocratic separations and gradient separations. Determining the average mobile phase density or average column pressure for an isocratic separation may be done by averaging the pressure measurements across the system, e.g., across the column and/or across any additional components which affect the density or pressure of the system. In a simple separation system configuration where the detector does not cause a significant density or pressure change in the system, the measurements may be taken upstream of and downstream of the column. These measurements are averaged to obtain the average mobile phase density or average column pressure for an isocratic separation.

Determining the average mobile phase density or average column pressure for a gradient separation may be done by averaging pressure measurements across the system taken at both the initial gradient conditions and the final gradient conditions. For example, a carbon dioxide based separation may use a gradient starting at 5% modifier in the carbon dioxide mobile phase and ending at 40% modifier. Preferably, the gradient is linear and continuous. Measurements are made at the initial conditions, i.e., 5% modifier. For instance, the backpressure regulator pressure value may be 2,000 psi and the pressure value upstream of the column may be 3,500 psi. Additional measurements are made at the final conditions, i.e. 40% modifier. For instance, the backpressure regulator pressure value may be 2,000 psi and the pressure value upstream of the column may be 4,500 psi. The average measurement for the initial conditions (3,500 psi and 2,000 psi) is 2,750 psi. The average measurement for the final conditions (4,500 psi and 2,000 psi) is 3,250 psi. The average of these average measurements (2,750 psi and 3,250 psi) is 3,000 psi. Upon transferring the gradient separation to a second separation procedure on a second separation system, the second separation should be performed at an average column pressure of 3,000 psi. The average column pressure on the second separation system should be calculated using similar procedures described above depending on whether the second separation procedure is performed under isocratic or gradient conditions.

After the average mobile phase density or average column pressure for the first separation on the first system has been measured or determined, the second separation on the second system should be performed at the measured or determined average mobile phase density or average column pressure. Achieving the average mobile phase density or average column pressure on the second separation system may be accomplished by routine optimization. For example, system parameters may be incrementally changed after the second separation system has equilibrated and adjusted toward the predetermined average mobile phase density or average column pressure measured or determined for the first separation on the first system. One advantage of the present disclosure is that optimization is focused on one main parameter, e.g., average mobile phase density or average column pressure, for optimizing the second separation on the second system, e.g., by iteration, rather than by optimizing all variables by trial and error. The average mobile phase density or average column pressure on the second separation system may also be achieved by using a controller.

In another embodiment, the present disclosure relates to a carbon dioxide based separation system comprising a pump, a column located downstream of the pump, a back pressure regulator located downstream of the column, at least two density or pressure sensors, one located upstream of the column and one located downstream of the column for measuring the average mobile phase density or pressure, and a density or pressure controller in communication with the at least two sensors capable of adjusting system parameters to achieve a pre-determined average mobile phase density or pressure in response to density or pressure measurements from the at least two sensors. The number and location of the sensors may be adjusted based on the presence of additional components, e.g., detector, that may cause a substantial density or pressure drop in the system. Additional sensors may be present to measure the density or pressure upstream, across and downstream of these components, as well. In a simple system, only two sensors (pressure or density) are required. Ideally, these sensors are located at the inlet and outlet of the column. Pressure drop between the pump and column inlet is minimal. Similarly, the pressure drop between the column outlet and ABPR is minimal. These sensors may also be located at the pump outlet and ABPR. For example, the system pressure sensor and the ABPR sensor may be used.

The controller may be any device capable of receiving signals from one or more pressure or density sensors, performing calculations using the received signals and sending signals to at least one system component to affect the component or a system parameter. The calculations performed by the controller may be simple (e.g., adding, subtracting, averaging) or complex (e.g., application of non-linear equation). In one embodiment, the calculation may be used to determine the average mobile phase density using system parameters, e.g., pressures and temperature, under conditions where there are inherent non-linear density properties of carbon dioxide. These calculations may be based on a multidimensional lookup or a single equation, pressure (temperature, average pressure, pressure drop), pressure (temperature, inlet pressure, outlet pressure) or an averaging integral of the pressure with respect to temperature and density. The equations and calculations are based on the known properties of carbon dioxide in the region of operation. The calculations and signal control are, in part controlled by the set of instructions, e.g., code or software. The set of instructions may be modified by the user for custom control over the chromatographic system. These may include items such as the system configuration to account for tubing pressure drops, column temperature to calculate density, and other system configuration or method related parameters. These parameters are use to more accurately model or calculate the mobile phase properties in the column.

In carbon dioxide based chromatographic systems, carbon dioxide properties vary throughout. To optimize the consistency of the separation, the controller should be controlling, at least, the property of interest at the point of interest. In most cases, this is the average solvating power (elutropic strength) in the column. In one embodiment, the at least one system component or parameter adjusted is the back pressure regulator. The back pressure regulator may be adjusted to a produce a higher pressure in the system if the average mobile phase density or pressure value is lower than the pre-determined average mobile phase density or pressure. In addition, the back pressure regulator may be adjusted to a produce a lower pressure in the system if the average mobile phase density or pressure value is higher than the pre-determined average mobile phase density or pressure. Adjusting the back pressure regulator may involve changing the pressure set point to change the average system pressure.

Existing systems control temperature at the column and pressure at the end of the system. Direct control of the properties of the system or in the column is not available. The present disclosure allows for control over these parameters, e.g. mobile phase density and system pressure. By controlling these parameters, more consistent analyte behavior is obtained. The controller may be configured to adjust the system parameters, e.g., pressure or temperature, at various locations based on sensor readings to automatically or contiguously adjusting the parameters to obtain the desired average mobile phase density or average column pressure. The adjustments, prior to obtaining the desired average mobile phase density or average column pressure, may be made prior to the system reaching equilibrium. For example, the system may monitor the average column pressure:

$$\text{Average Column Pressure} = [(\text{System Pressure at Pump} + \text{ABPR Pressure})/2],$$

and automatically adjust the ABPR setting to maintain the average column pressure at a constant value.

In one embodiment, the mobile phase density or pressure in the system is at equilibrium when the first and second mobile phase density or pressure measurements are measured by the first and second sensors. In another embodiment, the mobile phase density or pressure in the system is at equilibrium when the at least one system component or parameter is adjusted. In another embodiment, the mobile phase density or pressure in the system is not at equilibrium when the first and second mobile phase density or pressure measurements are measured by the first and second sensors. In yet another embodiment, the mobile phase density or pressure in the system is not at equilibrium when the at least one system component or parameter is adjusted.

Controlling the average mobile phase density or average column pressure makes carbon dioxide based chromatography scalable. An analyte's retention time, and other behavior, is also related to temperature since mobile phase density is a factor of both temperature and pressure. In some embodiments, the temperature of the separation system (e.g., the column) is controlled to achieve or maintain the average mobile phase density or average column pressure. The controller may have the ability to control the column or system temperature to achieve or maintain a consistent or pre-determined density or pressure value. In one embodiment, the apparatus and methods of the present disclosure comprise one or more temperature sensors for determining the temperature of the separation system, or more particularly for determining the temperature of the mobile phase at any given location in the separation system (e.g., column inlet, column outlet) as well as determining the column temperature. In other embodiments, the apparatus and methods of the present disclosure comprise one or more separation system heaters (e.g., column heater) to adjust the temperature of the system. The system or column temperature may be set using software or hardware settings, commanded using software or a temperature program or determined using one or more temperature sensors. The temperature sensors and the heaters can be connected to and controlled by the controller, similar to the way pressure is controlled. In some embodiments, both the pressure and the temperature of the separation system are controlled to achieve or maintain the average mobile phase density or average column pressure. In one embodiment, the average mobile phase density is calculated from the first and second mobile phase pressure measurements and a column temperature.

The software for the controller may be incorporated into the software, programming, or operating system used to control or manage the chromatographic system, e.g. commercially available systems from Waters Technologies Corporation (Milford, Mass.) and branded as Convergence Manager for ACQUITY® UPC².

As described herein, the average mobile phase density may be either measured directly, calculated, or approximated using system pressure measurements. The average pressure profile may be used as a close approximation to duplicate average density profiles between separations. It is within the scope of the present disclosure to use actual density measurements or calculations of those densities, if and when such measurements or calculations are available, in the implementation of this methodology. In one embodiment the set of instructions is capable of calculating or estimating the average mobile phase density and adjusting the system to obtain the pre-determined density value.

The present disclosure has also been demonstrated to improve system robustness by compensating for minor differences in system pressures encountered between different systems. As described previously, any component of a system that alters the pressure may impact the separation. As an example, there may be small amount of pressure drop in the tubing between the column outlet and the detector. If, due to contamination, that tubing became partially obstructed, this would result in an increase in pressure drop across that piece of tubing, and could alter the overall pressure profile for this separation, and hence may alter the retention and selectivity of the analytes. Compensating for this increased pressure due to tubing obstruction by maintaining the average pressure, either manually or in an automatic fashion, may maintain the chromatographic integrity of this separation yielding results similar to the separation prior to the tubing obstruction.

The present disclosure is directed to controlling solvent parameters (e.g., density) in carbon dioxide based chromatographic systems, and related systems. In these systems, controlling density directly, or indirectly by controlling pressure and/or temperature, is one means of controlling analyte solubility (e.g., the solvating power of the mobile phase). In one aspect, the present disclosure relates to the control of the mobile phase's solvating power by the control of system parameters, such as density, pressure and/or temperature. In one embodiment, the present disclosure relates to a method of controlling mobile phase solvating power in a carbon dioxide based separation system, comprising determining an average mobile phase density or pressure in the system, optionally, determining an average mobile phase temperature in the system, comparing the average mobile phase density or pressure with a pre-determined average mobile phase density or pressure, optionally, comparing the average mobile phase temperature with a pre-determined average mobile phase temperature, and adjusting at least one system component or parameter to achieve the pre-determined average mobile phase density, pressure, or optionally temperature.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

EXAMPLES

Example 1

This example demonstrates the efficient transfer of a carbon dioxide based chromatographic method between two analytical scale systems wherein the difference between the systems is the column particle size.

A sample mixture containing caffeine (1), carbamazepine (2), uracil (3), hydrocortisone (4), prednisolone (5) and sulfanilamide (6) was separated on an analytical scale carbon dioxide based chromatography instrument (ACQUITY® UPC², available at Waters Technologies Corporation (Milford, Mass.)) using a BEH 2-EP® column (2.1× 150 mm, 1.7 µm particle size), available at Waters Technologies Corporation (Milford, Mass.). The separation was isocratic using a carbon dioxide mobile phase with 10% methanol modifier and performed at a flow rate of 1.4 mL/min and at 40° C. The separation was optimized using traditional means. The optimized separation, shown in FIG. 2a (top chromatograph), has an ABPR setting of 1,500 psi. Pressure sensors were placed upstream and downstream of the column. The average column pressure calculated from the two pressure sensors was 3,694 psi.

The separation procedure was then transferred to a second system identical to the first system with the exception of the column stationary phase particle size. The second system consisted of an analytical scale carbon dioxide based chromatography instrument (ACQUITY® UPC², available at Waters Technologies Corporation (Milford, Mass.)) using a BEH 2-EP® column (2.1×150 mm, 5 µm particle size), available at Waters Technologies Corporation (Milford, Mass.). The particle size of the second column was 5 µm, as opposed to 1.7 µm. All other system conditions were the same. The separation was isocratic using a carbon dioxide mobile phase with 10% methanol modifier and performed at a flow rate of 1.4 mL/min and at 40° C. Initially, the second separation was performed at the ABPR setting of the first system, i.e., 1,500 psi. The ABPR sets the system outlet pressure to maintain the mobile phase density. The same ABPR setting is used in some embodiments to initially duplicate the pressure regime of the first separation. This resulted in an average column pressure in the second system of 1,752 psi. The resulting chromatograph, shown in FIG. 2a (middle chromatograph), was sub-optimal. The retention factor for sulfanilamide, for example, increased from 10.3 to 15.7.

Figure 2B:
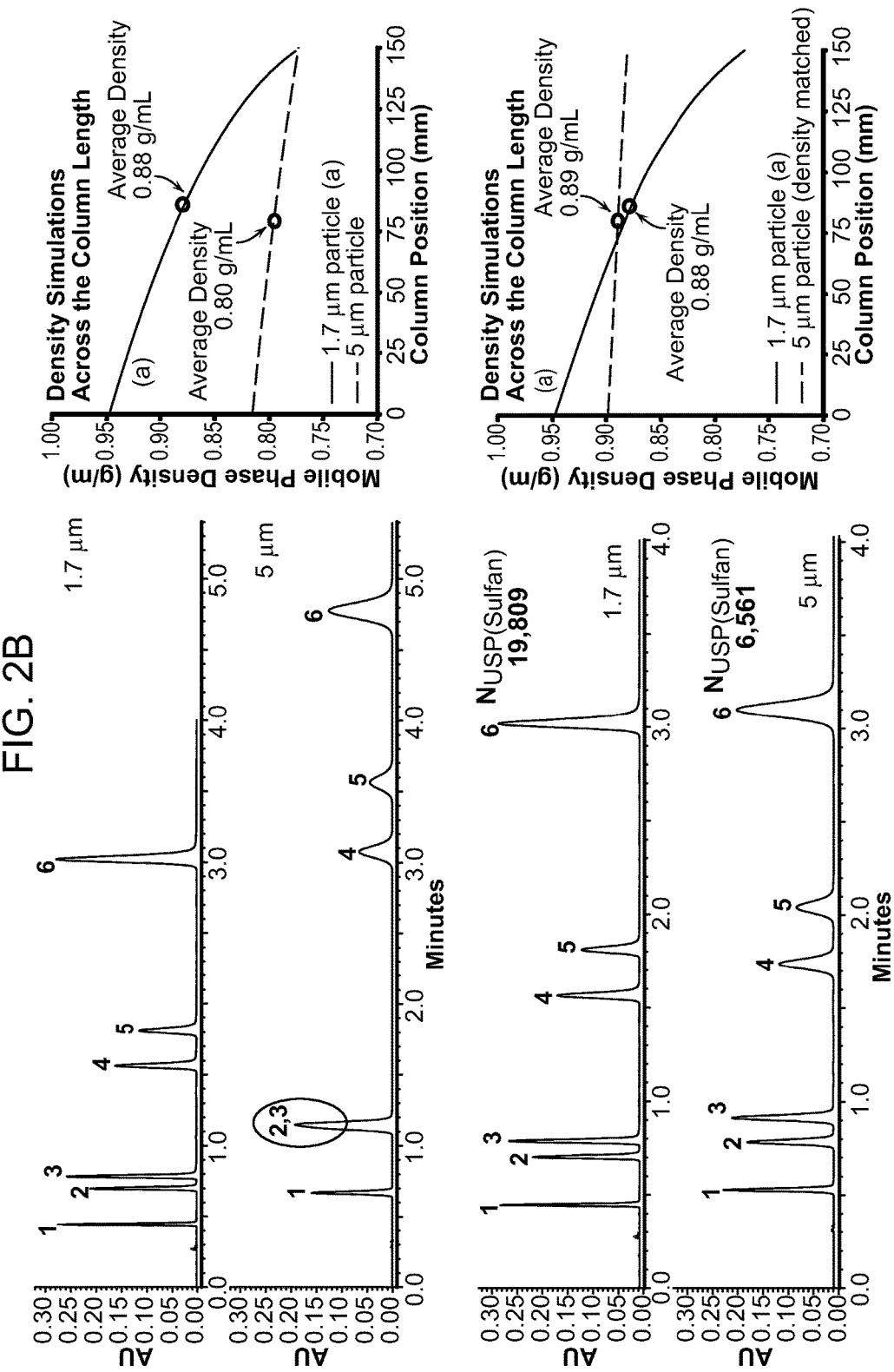
FIG. 2b shows a comparison of mobile phase density simulations across the column length with and without average density matching.

The pressure settings on the second system were incrementally adjusted so that the average column pressure for the second system (i.e., 3,693 psi) substantially matched the average column pressure of the first system (i.e., 3,694 psi). The final chromatograph, shown in FIG. 2a (bottom chromatograph), showed a separation similar to the optimized separation on the first system. The retention factors for sulfanilamide, for example, are comparable (10.3 vs. 9.2)—not shown. FIG. 2b shows a comparison of mobile phase density simulations across the column length with and without average density matching.

The use of the larger particle size, 5 µm, without adjustment of the ABPR, resulted in a lower pressure profile for the separation yielding different selectivity and retention factors relative to the initial 1.7 µm separation. The selectivity change is dramatic enough to result in a coelution of peaks 2 and 3. When the ABPR is adjusted to provide the similar separation pressure profile as the 1.7 µm separation, the resolution of peaks 2 and 3 is recovered, with similar selectivity and retention factors to the initial separation on the 1.7 µm particle. While the efficiency (N, number of theoretical plates) of the 5 µm separation is lower relative to the 1.7 µm separation, this is to be expected for the larger particle size, which is similar to what would be observed under conventional LC conditions.

Example 2

This example demonstrates the efficient transfer of a carbon dioxide based chromatographic method between two analytical scale systems wherein the difference between the systems is the column particle size and flow rate.

Figure 3:
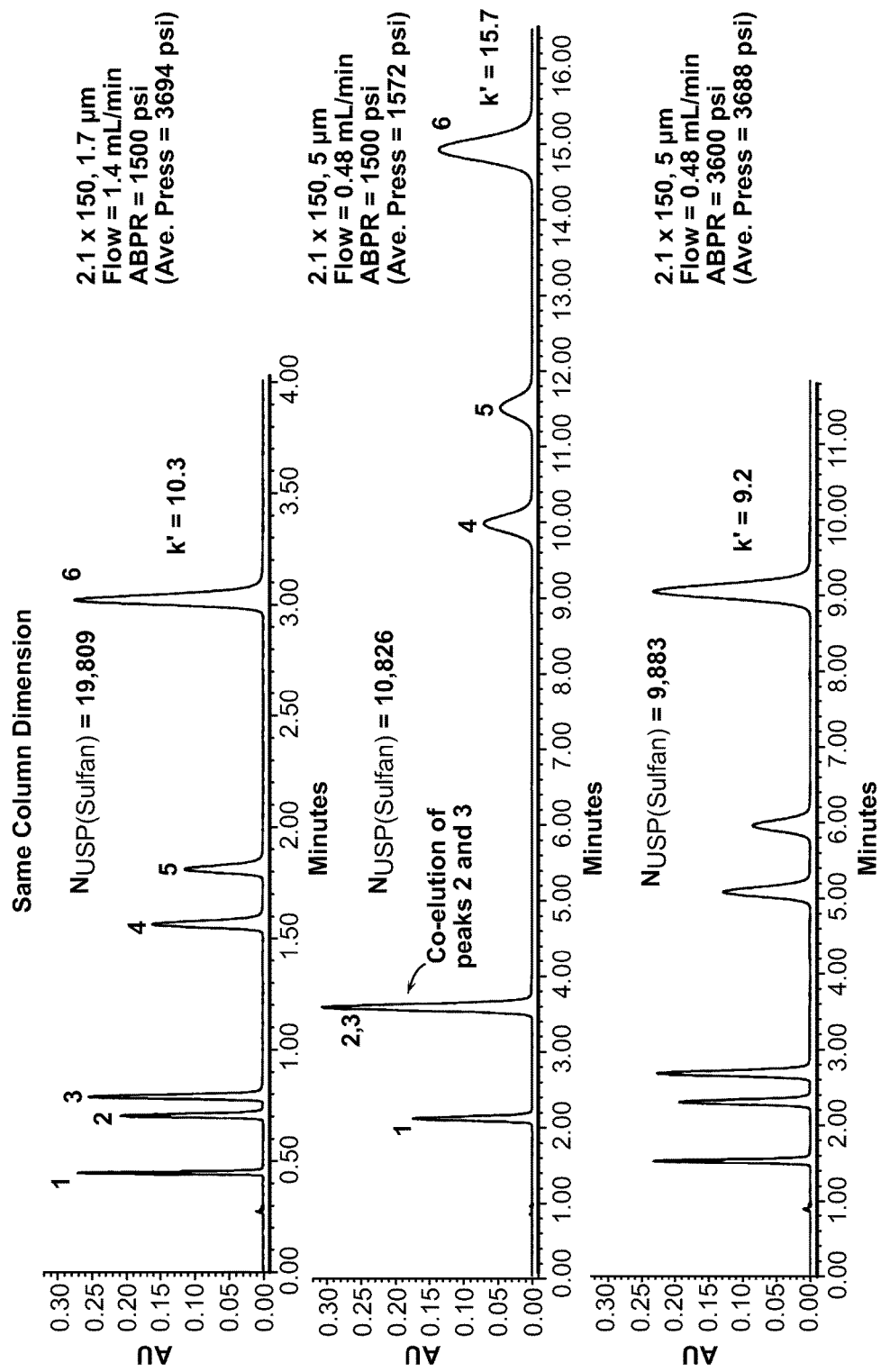
FIG. 3 demonstrates the transfer of a method developed on a 1.7 μm particle to a larger 5 μm particle, with and without matching the average density or average pressure profile for the separation, while scaling the flow rate to the lower optimum linear velocity for the 5 μm particle size.

The same sample mixture used in Example 1 was used. The first separation used the same procedure and separation system as used in Example 1. The first separation on the first system is shown in FIG. 3 (top chromatograph). The particle size was 1.7 µm. The flow rate was 1.4 mL/min. The ABPR was set to 1,500 psi. The average column pressure calculated from the two pressure sensors was 3,694 psi.

The separation procedure was then transferred to a second system identical to the first system with two exceptions, the column particle size and flow rate. The second system included a column having a 5 µm particle size and a flow rate of 0.48 mL/min. The flow rate was scaled to account for the difference in particle size to maintain the optimum linear velocity by adjusting the flow rate based on the ratio of the particle sizes:

flow rate×$(d_{p1}/d_{p2})$=1.4 mL/min×(1.7 µm/5 µm)=0.48 mL/min

Initially, the second separation was performed at the ABPR setting of the first system, i.e., 1,500 psi. This resulted in an average column pressure in the second system of 1,572 psi. The resulting chromatograph, shown in FIG. 3 (middle chromatograph), was sub-optimal. The retention factor for sulfanilamide, for example, increased from 10.3 to 15.7.

The pressure settings on the second system were incrementally adjusted so that the average column pressure for the second system (i.e., 3,688 psi) substantially matched the average column pressure of the first system (i.e., 3,694 psi). The final chromatograph, shown in FIG. 3 (bottom chromatograph), showed a separation similar to the optimized separation on the first system. The retention factors for sulfanilamide, for example, are comparable (10.3 vs. 9.2).

Example 3

This example demonstrates the efficient transfer of a carbon dioxide based chromatographic method between three analytical scale systems wherein the difference between the systems is the flow rate.

Figure 4A:
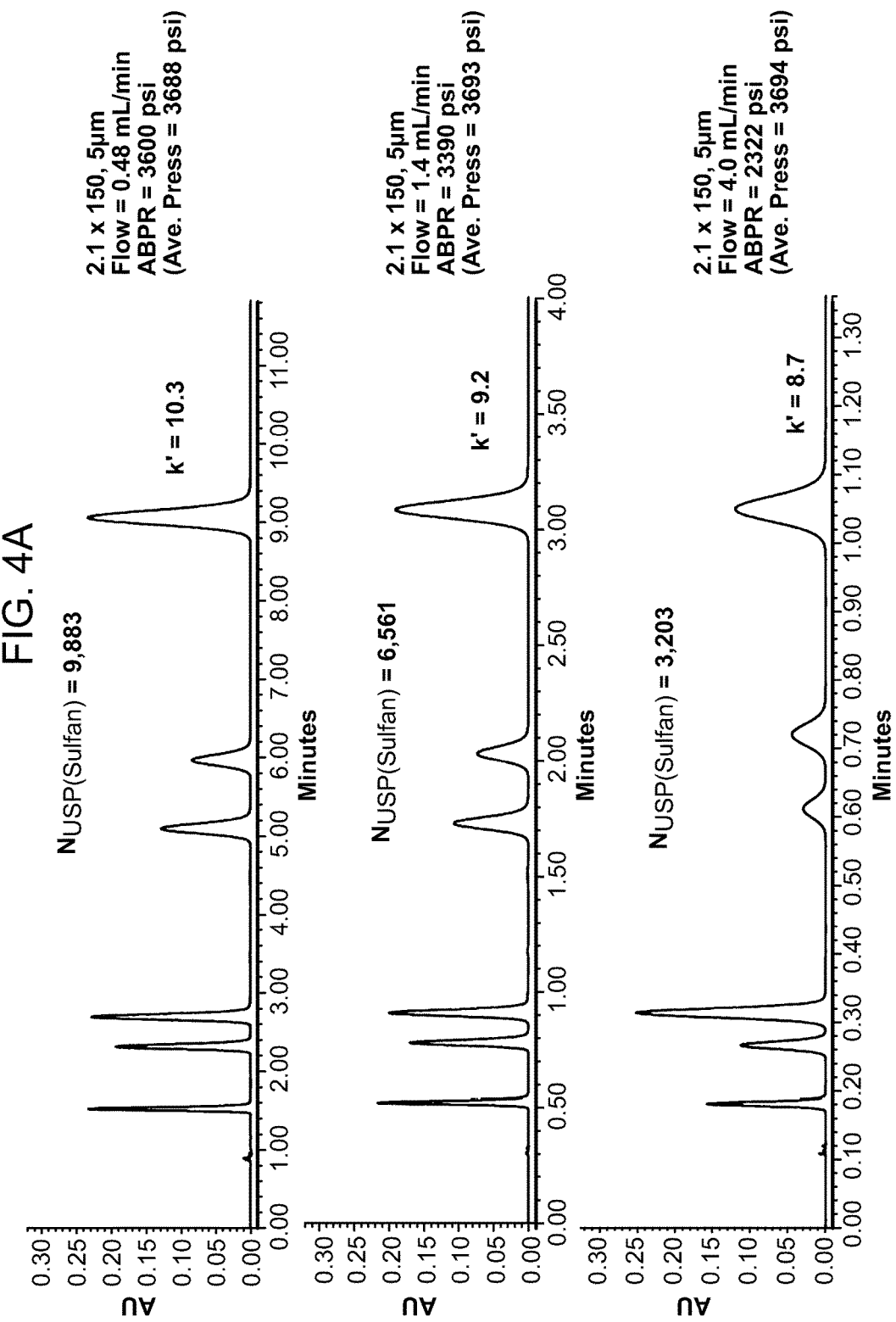
FIG. 4a shows a comparison of separations obtained on analytical scale carbon dioxide based chromatographic systems having the same average column pressure but different mobile phase flow rates, while matching the average density profiles for the separations. Without density matching, the changes in flow rates would result in significant differences in density profiles for the separations which would result in a loss of chromatographic integrity between the separations.

The same sample mixture used in Example 1 was used. The mixture was separated on an analytical scale carbon dioxide based chromatography instrument (ACQUITY® UPC$^2$, available at Waters Technologies Corporation (Milford, Mass.)) using a BEH 2-EP® column (2.1×150 mm, 5 µm particle size), available at Waters Technologies Corporation (Milford, Mass.). The separation was isocratic using a carbon dioxide mobile phase with 10% methanol modifier and performed at a flow rate of 0.48 mL/min and at 40° C. The separation was optimized using traditional means. The optimized separation, shown in FIG. 4a (top chromatograph), has an ABPR setting of 3,600 psi. The average column pressure calculated from the two pressure sensors was 3,688 psi.

The flow rate and ABPR were adjusted to evaluate the effect of different flow rates and ABPR settings for different separation procedures when the average column pressures is held constant. The flow rate was adjusted to 1.4 mL/min and the ABPR adjusted to 3,390 psi to achieve a substantially similar average column pressure (i.e., 3,693 psi) as the first system (3,688 psi). The resulting chromatograph, shown in FIG. 4a (middle chromatograph), showed a separation similar to the optimized separation on the first system. The retention factors for sulfanilamide, for example, are comparable (10.3 vs. 9.2).

Figure 4B:
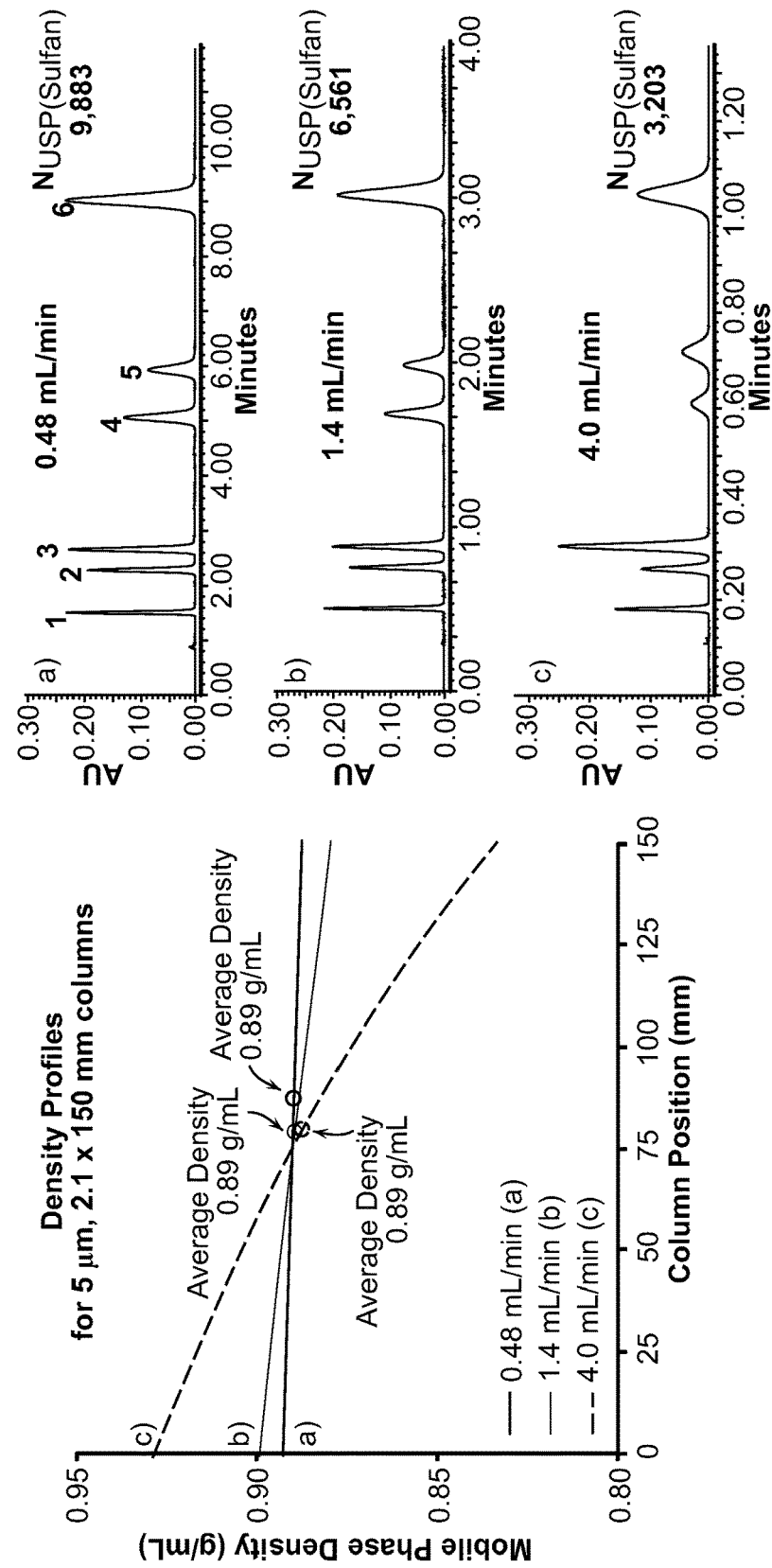
FIG. 4b shows a comparison of mobile phase density simulations across the column length with average density matching.

In another separation, the flow rate was adjusted to 4.0 mL/min and the ABPR adjusted to 2,322 psi to achieve a substantially similar average column pressure (i.e., 3,694 psi) as the first system (3,688 psi). The resulting chromatograph, shown in FIG. 4a (bottom chromatograph), showed a separation similar to the optimized separation on the first system and on the second system. The retention factors for sulfanilamide, for example, are comparable (10.3 vs. 9.2 vs. 8.7). As is similarly observed for LC methods, a decrease in overall separation efficiency (N) is observed at flow rates faster than the optimum linear velocity (~0.48 mL/min for a 5 µm particle size in this current configuration). FIG. 4b shows a comparison of mobile phase density simulations across the column length with average density matching.

Example 4

This example demonstrates the efficient transfer of a carbon dioxide based chromatographic method developed using an analytical scale instrument to a preparative SFC instrument.

Figure 5:
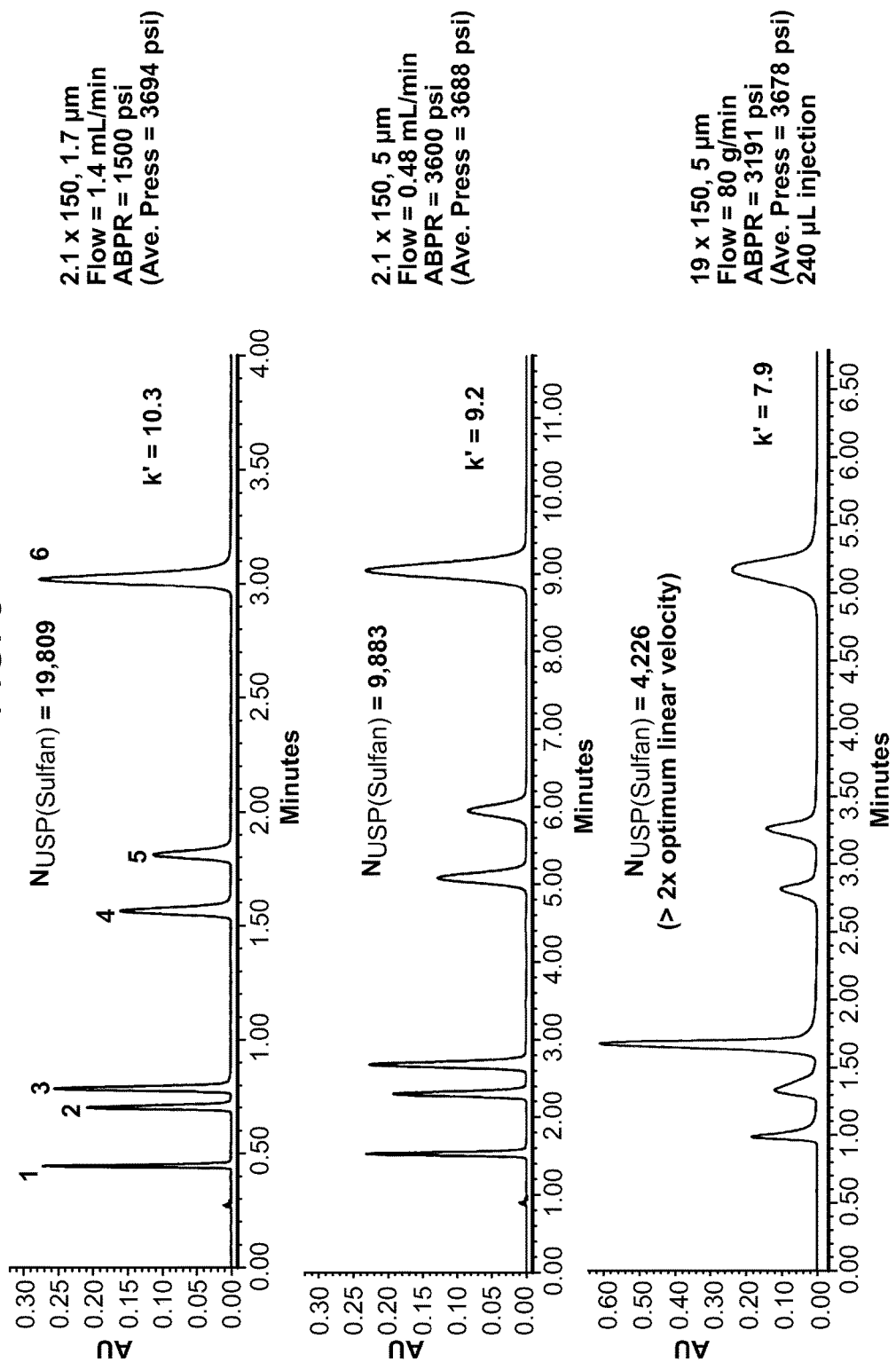
FIGS. 5 and 6 show a comparison of separations obtained on an analytical scale carbon dioxide based chromatographic system and a preparative scale carbon dioxide based chromatographic system having the same average column pressure.

The same sample mixture used in Example 1 was used. The initial separation used the same procedure and separation system as used in Example 1. The optimized separation, shown in FIG. 5 (top chromatograph), has an ABPR setting of 1,500 psi. The average column pressure calculated from the two pressure sensors was 3,694 psi.

The separation procedure was then transferred to a second system identical to the first system with two exceptions, the column particle size and flow rate. The second system included a column having a 5 µm particle size and a flow rate of 0.48 mL/min. (See Example 3). The final chromatograph in FIG. 3, shown in FIG. 5 (middle chromatograph), showed a separation similar to the optimized separation on the first system. The retention factors for sulfanilamide, for example, are comparable (10.3 vs. 9.2).

The separation procedure was then transferred a third system, i.e., a preparative scale carbon dioxide based chromatography instrument (Prep 100 SFC, available at Waters Technologies Corporation (Milford, Mass.)). The third system used the same column chemistry (BEH 2-EP®) as the previous separations but in a larger configuration (19×150 mm, 5 µm particle size), available at Waters Technologies Corporation (Milford, Mass.). The separation was isocratic using a carbon dioxide mobile phase with 6% methanol modifier and performed at a flow rate of 80 g/min and 40° C. While most analytical instrumentation measures flow volumetrically (mL/min), many preparative SFC instruments measure flow rate in mass with units of g/min. At the densities used for preparative chromatography, 80 g/min correlates to approximately 83 mL/min. The injection volume used for the preparative separation, 240 µL, was scaled from the analytical separation (2 µL injection volume) by the ratio of the column volumes for the two systems:

$$2 \text{ µL injection} \times (\text{Volume2}_{19 \times 150}/\text{Volume1}_{30 \times 50}) = 240 \text{ µL injection}$$

The pressure settings on the third system were incrementally adjusted so that the average column pressure for the third system (i.e., 3,678 psi) substantially matched the average column pressure of the first system (i.e., 3,694 psi). The chromatograph for the third system, shown in FIG. 5 (bottom chromatograph), showed a separation similar to the optimized separation on the first system and the second system. The retention factors for sulfanilamide, for example, are comparable (10.3 vs. 9.2 vs. 7.9).

Example 5

This example demonstrates the efficient transfer of a carbon dioxide based chromatographic method developed using an analytical scale instrument to a preparative SFC instrument.

Figure 6:
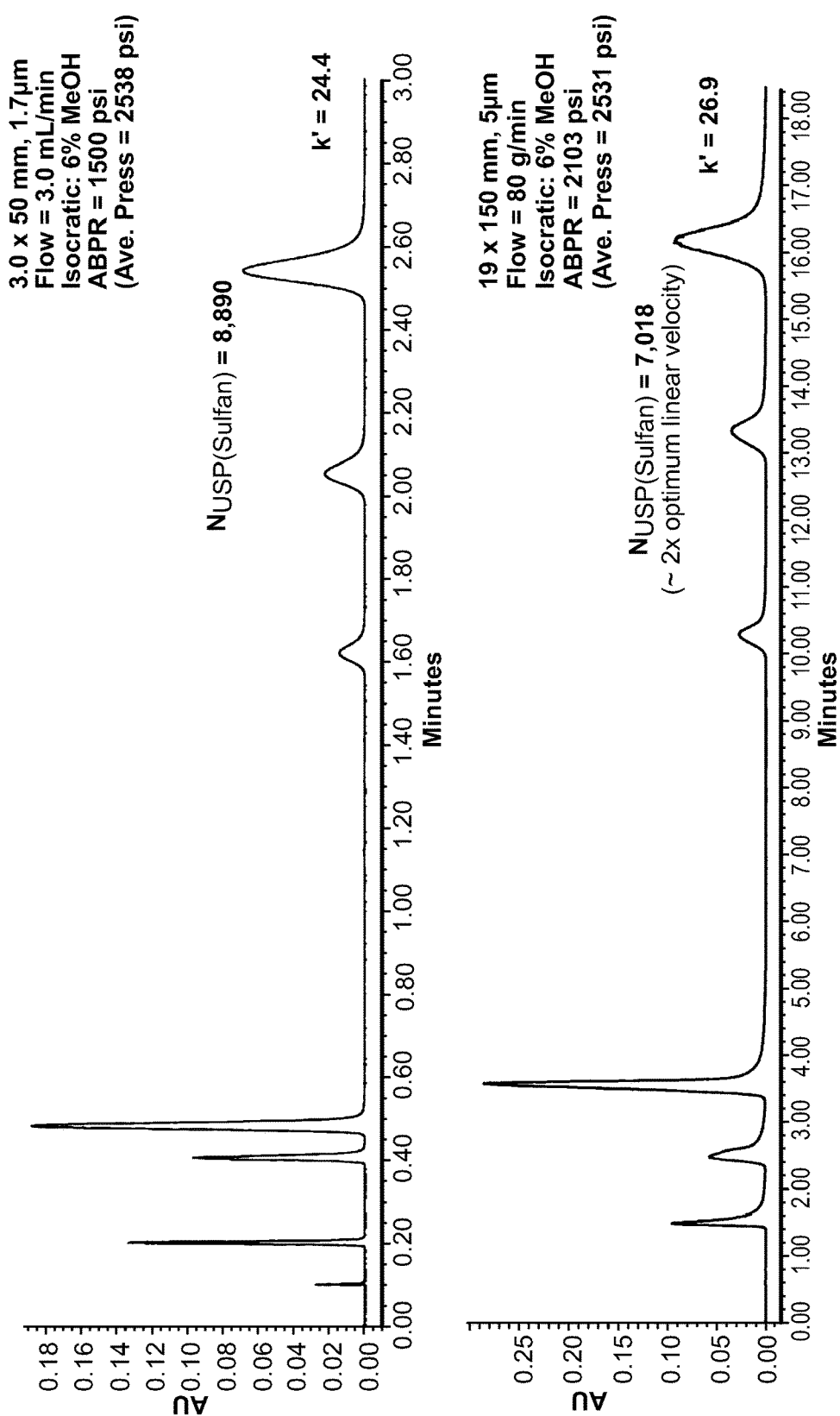

The same sample mixture used in Example 1 was used. The first system was an analytical scale carbon dioxide based chromatography instrument (ACQUITY® UPC$^2$, available at Waters Technologies Corporation (Milford, Mass.)) using a BEH 2-EP® column (3.0×50 mm, 1.7 µm particle size), available at Waters Technologies Corporation (Milford, Mass.). The separation was isocratic using a carbon dioxide mobile phase with 6% methanol modifier and performed at a flow rate of 3.0 mL/min and 40° C. The injection volume was 1 µL. The separation was optimized using traditional means. Pressure sensors were placed upstream and downstream of the column. The optimized separation, shown in FIG. 6 (top chromatograph), has an ABPR setting of 1,500 psi and a system pressure upstream of the column of 3,576 psi. The average column pressure calculated from the two pressure sensors was 2,538 psi.

The separation procedure was then transferred to a second system, i.e., a preparative scale carbon dioxide based chromatography instrument (Prep 100 SFC, available at Waters Technologies Corporation (Milford, Mass.)). As is common for the transfer of LC methods, the ratio of the column length to the particle size ($L/d_p$) was maintained using the same column chemistry, BEH 2-EP®, for the second system (3.0×50 mm, 1.7 µm column scaled to 19×100 mm, 5 µm particle size column), available at Waters Technologies Corporation (Milford, Mass.).

The separation was isocratic using a carbon dioxide mobile phase with 6% methanol modifier and performed at a flow rate of 80 g/min and 40° C. As in the previous example, the injection volume for the preparative separation was scaled to 240 µL. The pressure settings on the second system were incrementally adjusted so that the average column pressure for the second system (i.e., 2,531 psi) substantially matched the average column pressure of the first system (i.e., 2,538 psi). The chromatograph for the second system, shown in FIG. 6 (bottom chromatograph), showed a separation similar to the optimized separation on the first system. The retention factors for sulfanilamide, for example, are comparable (24.4 vs. 26.9).

For method transfer from analytical to preparative conditions, the ratio of column length to particle size for the two columns ($L/d_p$) was maintained, resulting in similar selectivity and retention factors after adjustment of the ABPR to maintain the same average pressure profile for the separation. It is not necessary, however, to match the column length/particle size ratio for the transfer of methods. Maintenance of this ratio yields the same efficiency between separations. In the current example, a 100 mm column could have been used with fairly good success, although with less efficiency than the original separation. The efficiency difference that is observed can be attributed, in part, to the difference in particle size and the faster linear velocity used for the preparative system relative to the analytical separation. This ability enables the rapid screening of methods on the faster analytical scale, with the direct transfer of the final method to preparative chromatography, resulting in significant savings in time and mobile phases.

Example 6

This example demonstrates the effect of injection volume and sample concentration on the separation performance of a carbon dioxide based chromatographic method at a constant average column pressure.

Figure 7:
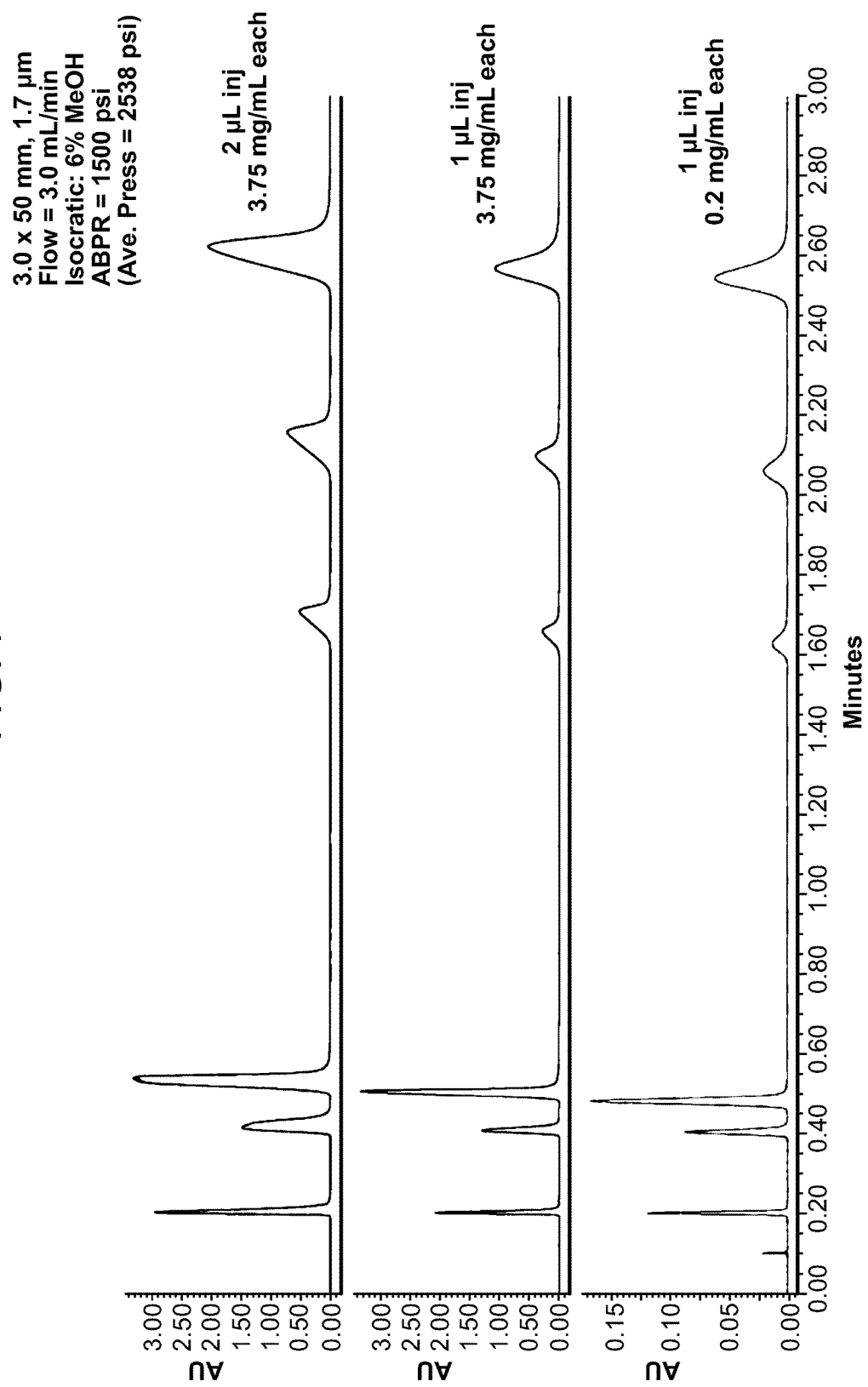
FIG. 7 shows a comparison of separations obtained on the same analytical scale carbon dioxide based chromatographic system having the same average column pressure but different injection volumes and sample analyte concentrations.

The same sample mixture used in Example 1 is used. The mixture was separated on an analytical scale carbon dioxide based chromatography instrument (ACQUITY® UPC$^2$, available at Waters Technologies Corporation (Milford, Mass.)) using a BEH 2-EP® column (3.0×50 mm, 1.7 µm particle size), available at Waters Technologies Corporation (Milford, Mass.). The separation was isocratic using a carbon dioxide mobile phase with 6% methanol modifier and performed at a flow rate of 3.0 mL/min and at 40° C. The injection volume was 1 µL. The concentration of each analyte in the mixture was 0.2 mg/mL. The separation was optimized using traditional means. The optimized separation, shown in FIG. 7 (bottom chromatograph), has an ABPR setting of 1,500 psi. Pressure sensors were placed upstream and downstream of the column. The average column pressure calculated from the two pressure sensors was 2,538 psi.

The separation was repeated using a different separation procedure. The concentration was adjusted to 3.75 mg/mL. The average column pressure remained constant at 2,538 psi. The resulting separation, shown in FIG. 7 (middle chromatograph), showed a similar separation. The separation was also repeated using another separation procedure. The injection volume was adjusted to 2 µL and the sample concentration was adjusted to 3.75 mg/mL each. The average column pressure remained constant at 2,538 psi. The resulting separation, shown in FIG. 7 (top chromatograph), showed a similar separation. Changes in injection volume and sample concentration appear to have little effect on the separation performance of an SFC method at a constant average column pressure.

Example 7

This example demonstrates the calculation of the average column pressure for a gradient separation for a carbon dioxide based chromatographic separation.

Figure 8:
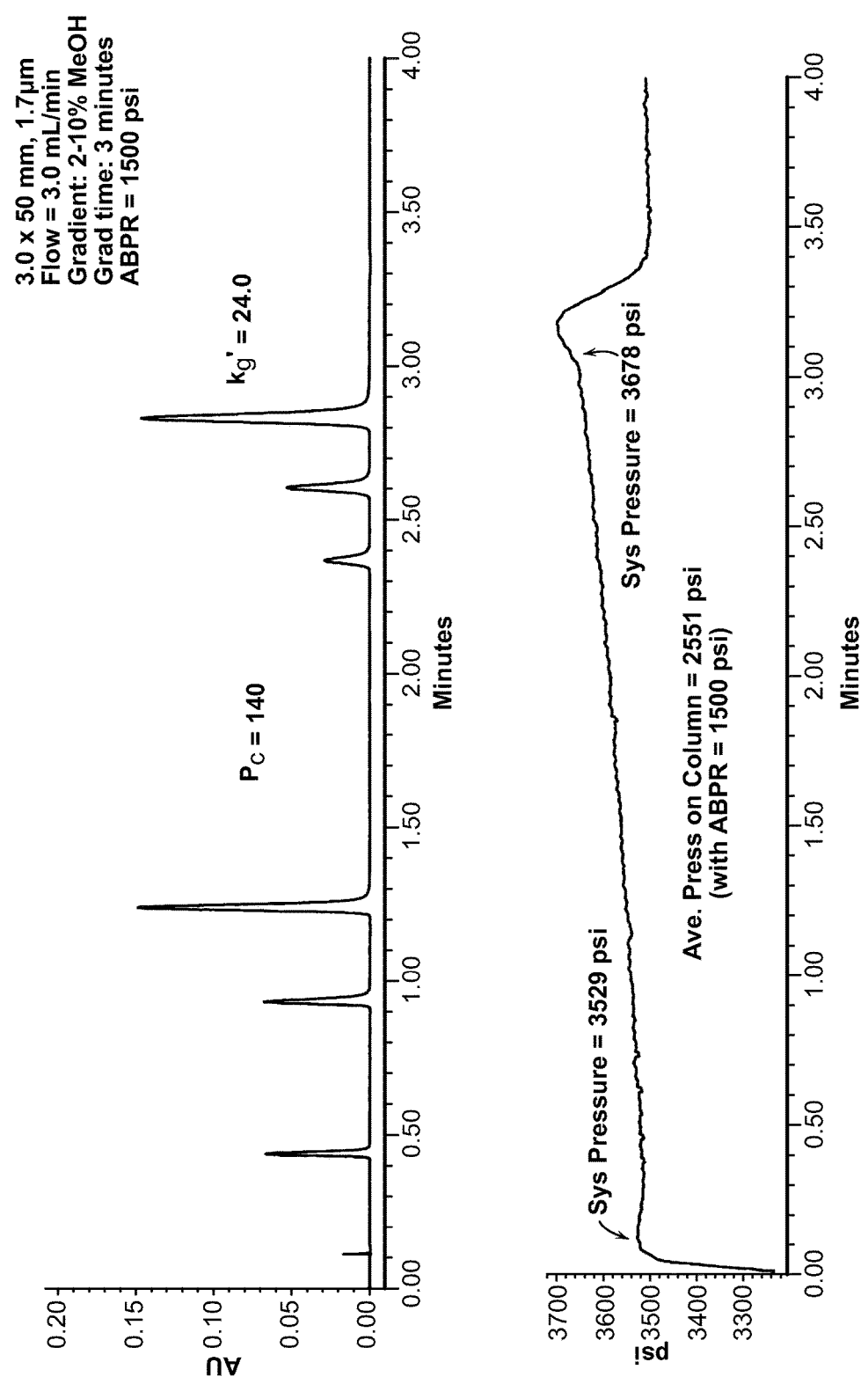
FIG. 8 shows a gradient separation on an analytical scale carbon dioxide based chromatographic system.

The same sample mixture used in Example 1 is used. The mixture was separated on an analytical scale carbon dioxide based chromatography instrument (ACQUITY® UPC$^2$, available at Waters Technologies Corporation (Milford, Mass.)) using a BEH 2-EP® column (3.0×50 mm, 1.7 μm particle size), available at Waters Technologies Corporation (Milford, Mass.). The separation used a carbon dioxide mobile phase with 2-10% methanol modifier adjusted under gradient conditions over 3 minutes. The flow rate was 3.0 mL/min. The separation was optimized using traditional means. The optimized separation, shown in FIG. 8 (top chromatograph), has an ABPR setting of 1,500 psi. Pressure sensors were placed upstream and downstream of the column. The system pressure readings are shown in FIG. 8, (bottom trace). At the initial gradient conditions, i.e., 2% modifier, the system pressure upstream of the column was 3,529 psi and the system pressure downstream of the column was 1,500 psi. The average column pressure was calculated at the initial gradient conditions as 2,514 psi, which is the average of 3,529 psi and 1,500 psi. At the final gradient conditions, i.e., 10% modifier, the system pressure upstream of the column was 3,678 psi and the system pressure downstream of the column was 1,500 psi. The average column pressure was calculated at the final gradient conditions as 2,589 psi, which is the average of 3,678 psi and 1,500 psi. Thereafter, the average column pressure for the gradient separation was calculated to be 2,551 psi, which is the average of 2,514 psi and 2,589 psi.

Example 8

This example demonstrates the effect of injection volume and sample concentration on the gradient separation performance of a carbon dioxide based chromatographic method at a constant average column pressure.

Figure 9:
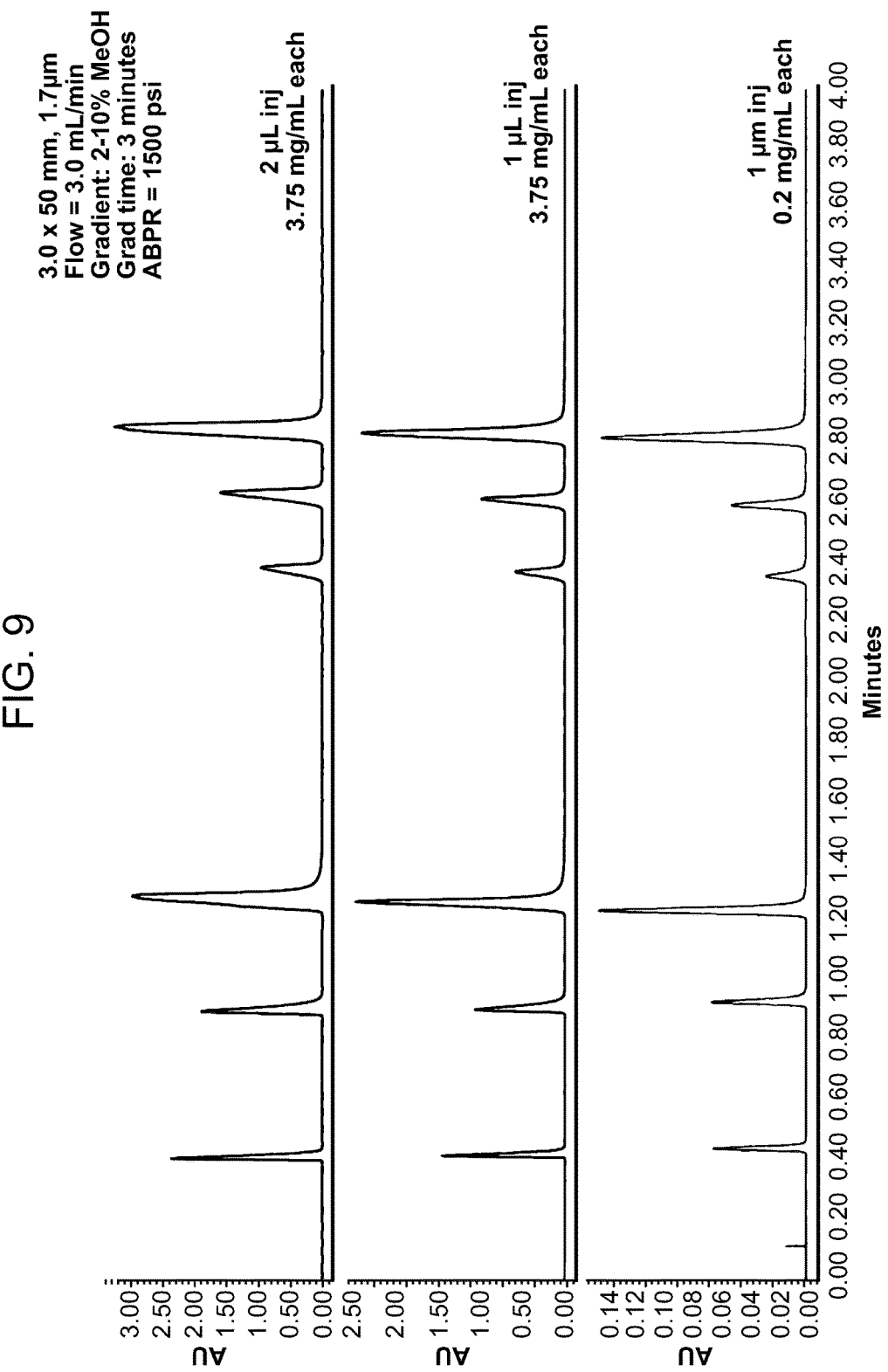
FIG. 9 shows a comparison of gradient separations obtained on the same analytical scale carbon dioxide based chromatographic system having the same average column pressure but different injection volumes and sample analyte concentrations.

The same sample mixture used in Example 1 is used. The mixture was separated on an analytical scale carbon dioxide based chromatography instrument (ACQUITY® UPC$^2$, available at Waters Technologies Corporation (Milford, Mass.)) using a BEH 2-EP® column (3.0×50 mm, 1.7 μm particle size), available at Waters Technologies Corporation (Milford, Mass.). The separation used a carbon dioxide mobile phase with 2-10% methanol modifier adjusted under gradient conditions over 3 minutes. The flow rate was 3.0 mL/min. The injection volume was 1 μL. The concentration of the analytes in the mixture was 0.2 mg/mL each. The separation was optimized using traditional means. The optimized separation, shown in FIG. 9 (bottom chromatograph), has an ABPR setting of 1,500 psi. Pressure sensors were placed upstream and downstream of the column.

The separation was repeated using a different separation procedure. The concentration was adjusted to 3.75 mg/mL. The average column pressure remained constant. The resulting separation, shown in FIG. 9 (middle chromatograph), showed a similar separation. The separation was also repeated using another separation procedure. The injection volume was adjusted to 2 μL and the sample concentration was adjusted to 3.75 mg/mL each. The resulting separation, shown in FIG. 9 (top chromatograph), showed a similar separation. Changes in injection volume and sample concentration appear to have little effect on the separation performance of a gradient SFC method at a constant average column pressure.

Example 9

This example demonstrates the efficient transfer of a gradient carbon dioxide based chromatographic method developed using an analytical scale instrument to a preparative carbon dioxide based chromatographic instrument.

Figure 10:
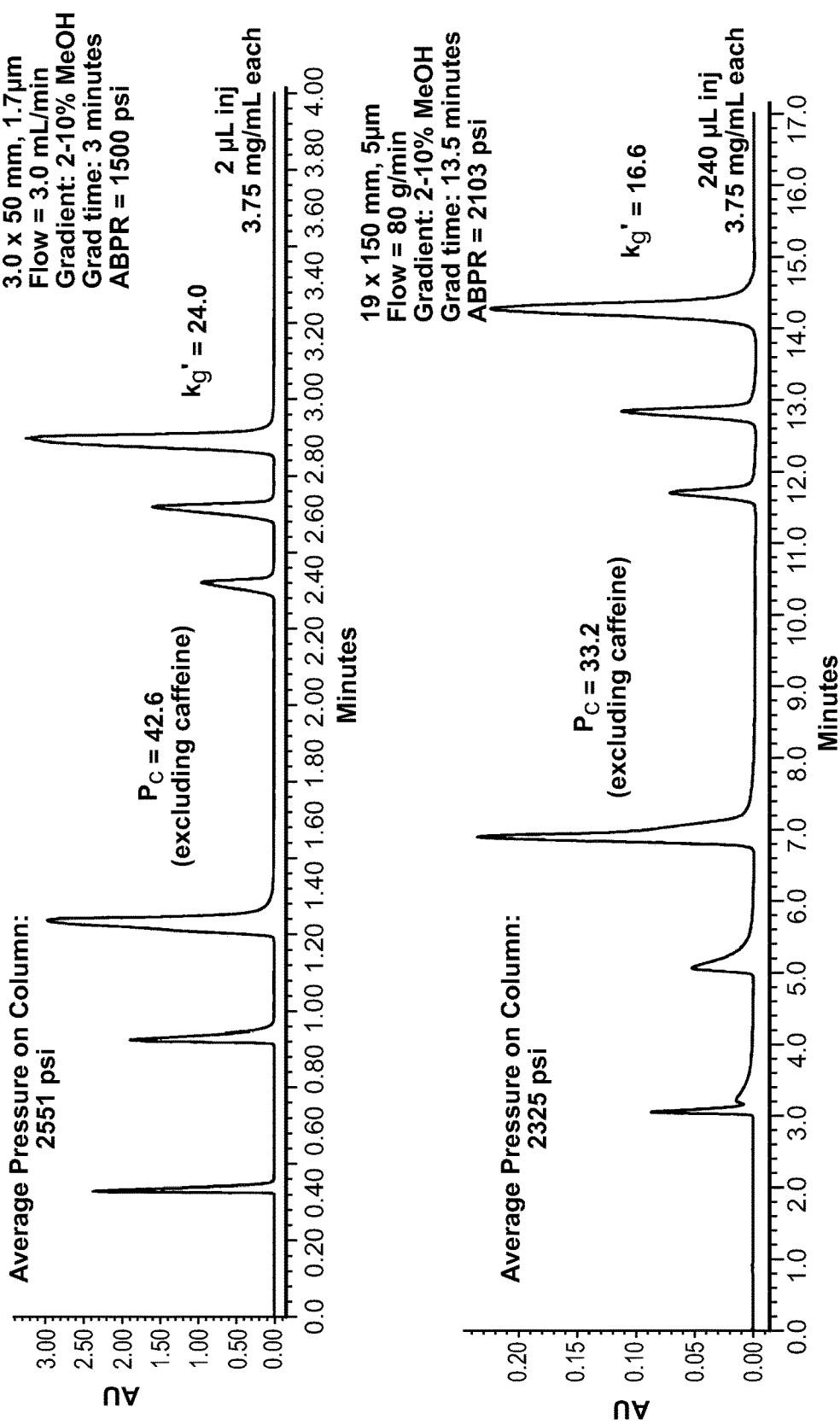
FIG. 10 shows a comparison of gradient separations obtained on an analytical scale carbon dioxide based chromatographic system and a preparative scale carbon dioxide based chromatographic system having similar average column pressures.

The same sample mixture used in Example 1 was used. The initial separation used the same procedure and separation system as used in Example 7. The optimized separation, shown in FIG. 10 (top chromatograph), has an ABPR setting of 1,500 psi. The average column pressure calculated from the two pressure sensors was 2,551 psi.

The separation procedure was then transferred to a second system, i.e., a preparative scale carbon dioxide based chromatography instrument (Prep 100 SFC, available at Waters Technologies Corporation (Milford, Mass.)). The second system used the same column chemistry (BEH 2-EP®) as the previous separations but in a larger configuration (19× 150 mm, 5 μm particle size), available at Waters Technologies Corporation (Milford, Mass.). The separation used a carbon dioxide mobile phase with a 2-10% methanol modifier gradient over 13.5 minutes. The gradient time of 13.5 minutes was scaled from the original conditions (3 minutes at 3 mL/min) to maintain the same number of column volumes of mobile phase during the gradient at a flow rate of approximately 83 mL/min. The injection volume was 240 μL. The pressure settings on the second system were incrementally adjusted so that the average column pressure for the second system (i.e., 2,325 psi) roughly matched the average column pressure of the first system (i.e., 2,551 psi). The chromatograph for the second system, shown in FIG. 10 (bottom chromatograph), showed a separation similar to the optimized separation on the first system. The retention factors for sulfanilamide, for example, are comparable (24.0 vs. 16.6). The discrepancy in retention factors observed here are primarily due to differences in overall system volume between the two systems that were not corrected for in these evaluations.

Example 10

This example demonstrates the effect of flow rate on k' for systems maintaining a constant system pressure.

The same sample mixture and separation system described in Example 1 was used. Separations were performed using both a low back pressure column (about 300 psi delta) and a high back pressure column (about 2,000 psi delta). The result for each column was the same.

Figure 11:
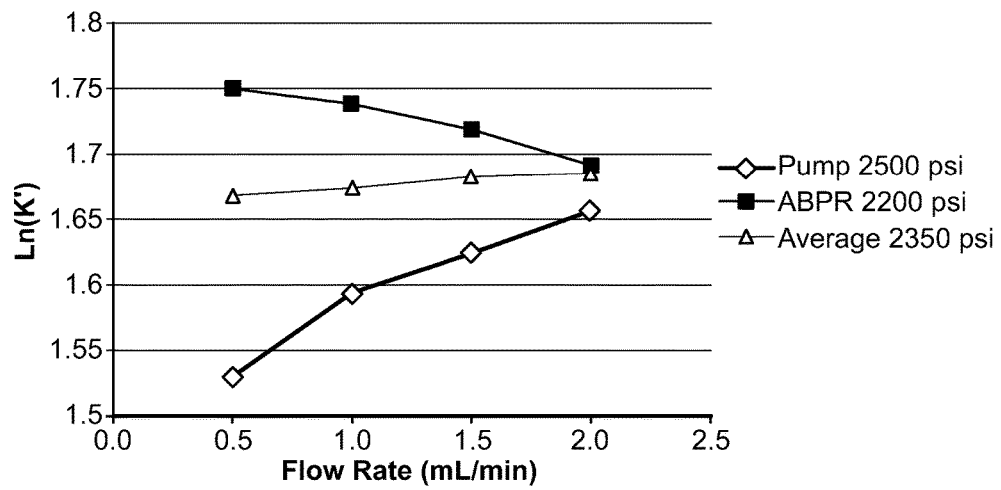
FIGS. 11 and 12 show a comparison of k' values for two different carbon dioxide based chromatographic systems under different pressure conditions.
Figure 12:
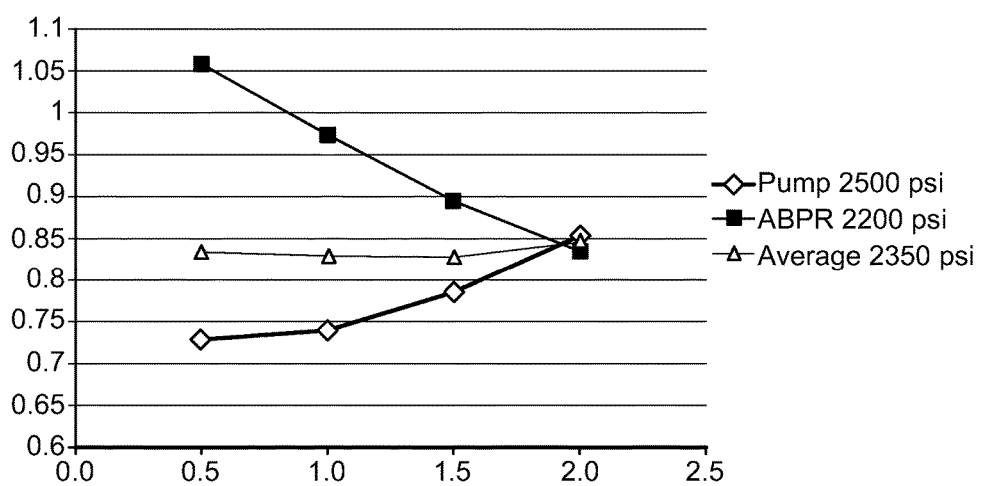

For each system, the separation was performed for three different pressure scenarios. The first scenario maintained a constant pressure at the pump of about 2,500 psi as the flow rate was varied from 0.5 mL/min to 2 mL/min. To maintain the system pressure at a constant value, the ABPR pressure setting was decreased to compensate for the higher pressures at the higher flow rates. The second scenario maintained a constant pressure at the ABPR of about 2,200 psi as the flow rate was varied from 0.5 mL/min to 2 mL/min. Under these conditions, the system pressure increased as a consequence of the increasing flow rate. The third scenario maintained a constant average pressure across the column of about 2,350 psi as the flow rate was varied from 0.5 mL/min to 2 mL/min. The results are shown in FIGS. 11 and 12. The k' value for peak 3 (uracil) is representative of performance for the other analytes. As shown, by maintaining a constant average pressure across the column the k' values remain almost constant. The variation in k' observed may be caused by the pressure drop through the tubing not being accounted for in the average pressure. By maintaining a constant pressure at only one point in the system, e.g., pump or ABPR, the system pressure for the first two settings does not remain constant.

Maintaining a constant k' for each analyte over various flow rates also allows for control over the separation time. A constant k' for each analyte keeps the analytes from moving relative to each other and maintains the elution order. Separations may be performed more quickly. The transfer of methods between two system may also be faster.

Example 11

This example demonstrates the effect on analyte retention in response to small changes in system pressure. These small changes in system pressure can be a result of system to system variation, they can be introduced intentionally, by changes in tubing i.d or length, or they can be unintentional and often times not obvious. This could be the result of a contaminant lodged in the system which causes a small restriction of the flow path resulting in small increases in operating pressure. It could also be the result of a very small leak causing a decrease in the overall operating pressure. Often times these issues are difficult to identify and can result in chromatographic inconsistencies from system to system or over time.

Figure 13:
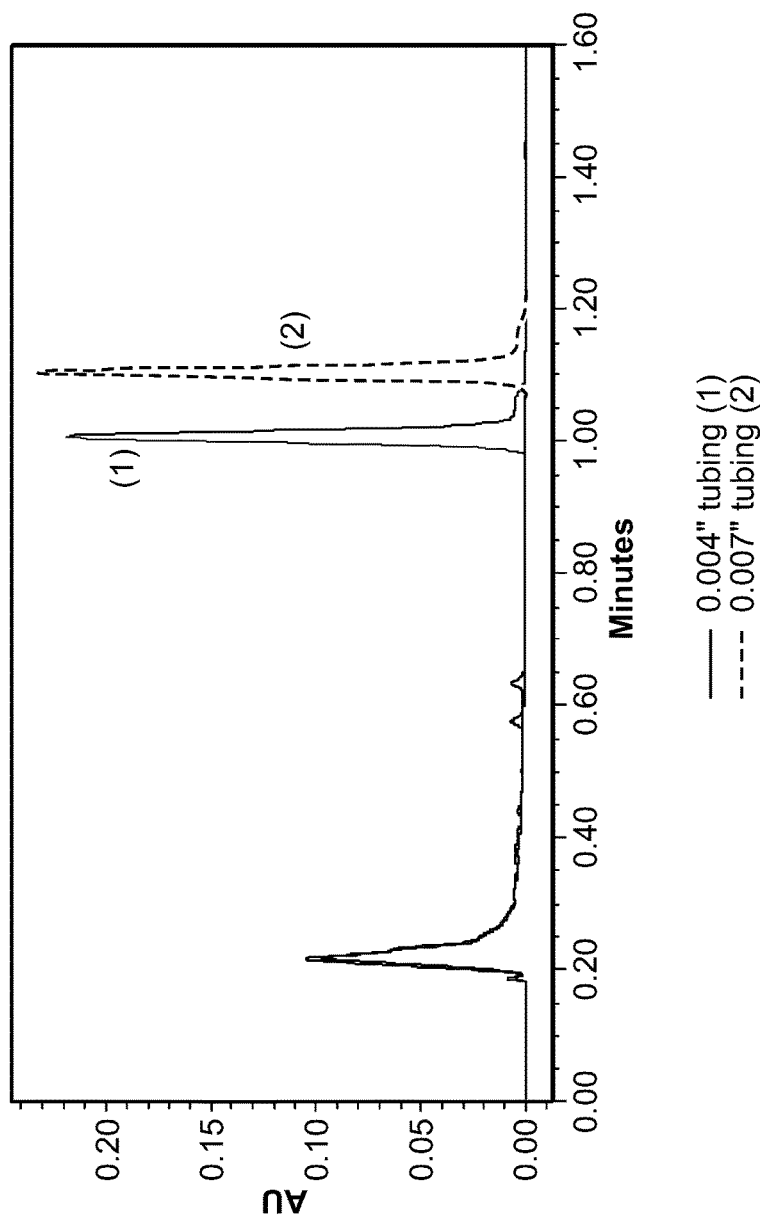
FIGS. 13 and 14 show the effect on analyte retention in response to small changes in system pressure, and the correlation of those effects by matching the pressure profiles for the separation.
Figure 14:
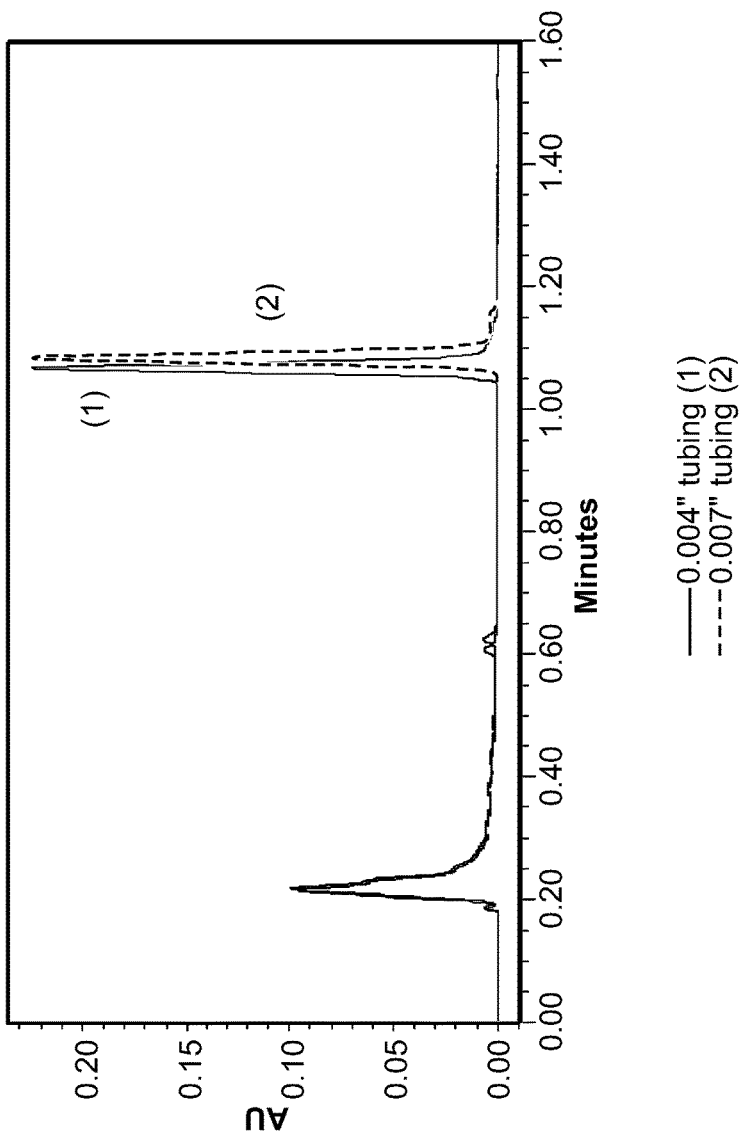

Using the current methodology of matching average density or average column pressure profiles can mitigate the changes in retention due to these small changes in system pressure. FIGS. 13 and 14 demonstrate this concept for a change in system tubing. The column outlet tubing, with a 0.007" ID, was substituted with a new piece of tubing with a 0.004" ID. The reduction in tubing ID resulted in a 400 psi increase in overall system pressure. The impact of this pressure increase can be seen in the FIG. 13 in which the peak collected at the higher pressure, with the smaller ID tubing, is shifted to lower k' values. This shift in retention can be mitigate by maintaining the average column pressure, shown in FIG. 14, resulting in peaks with nearly identical retention factors.

Example 12

This example demonstrates the effect on analyte retention factor and selectivity in response to changes in system density.

Figure 15B:
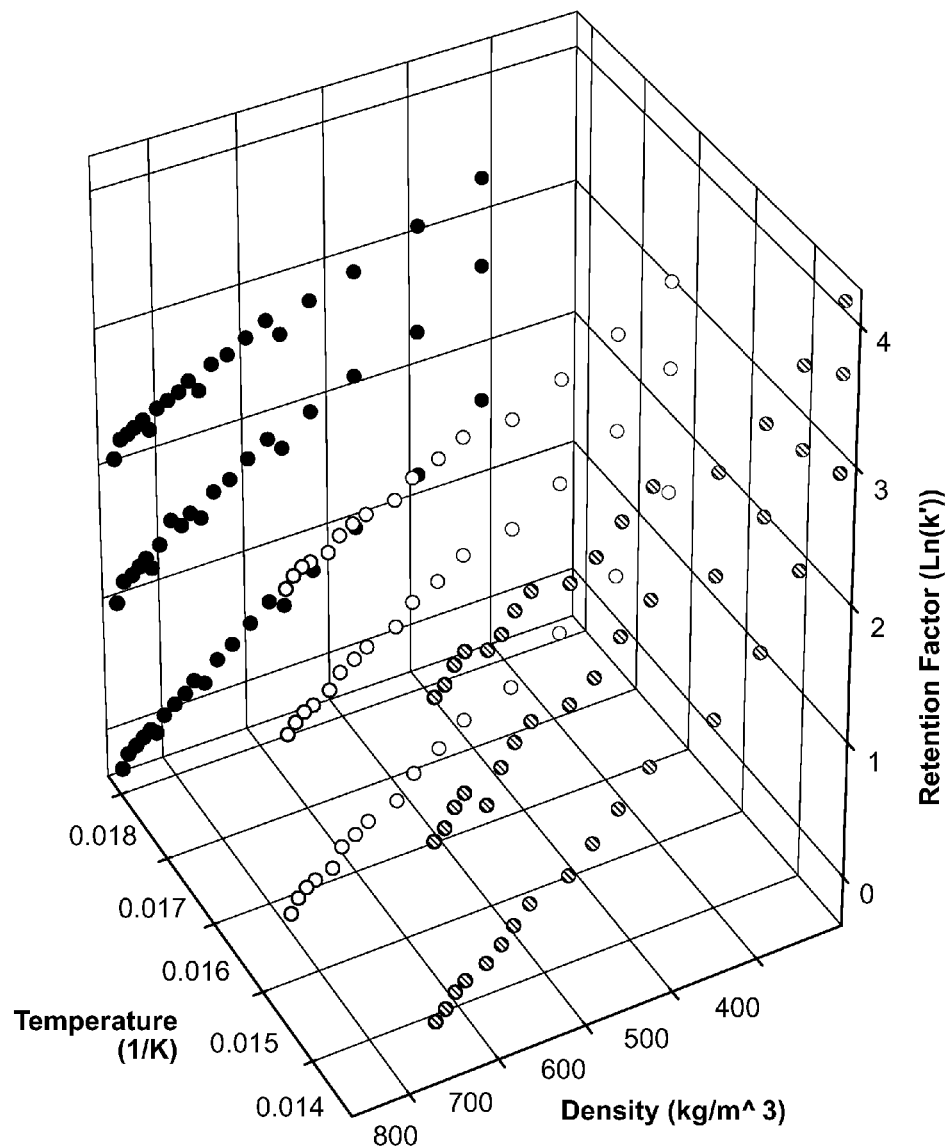
Figure 16A:
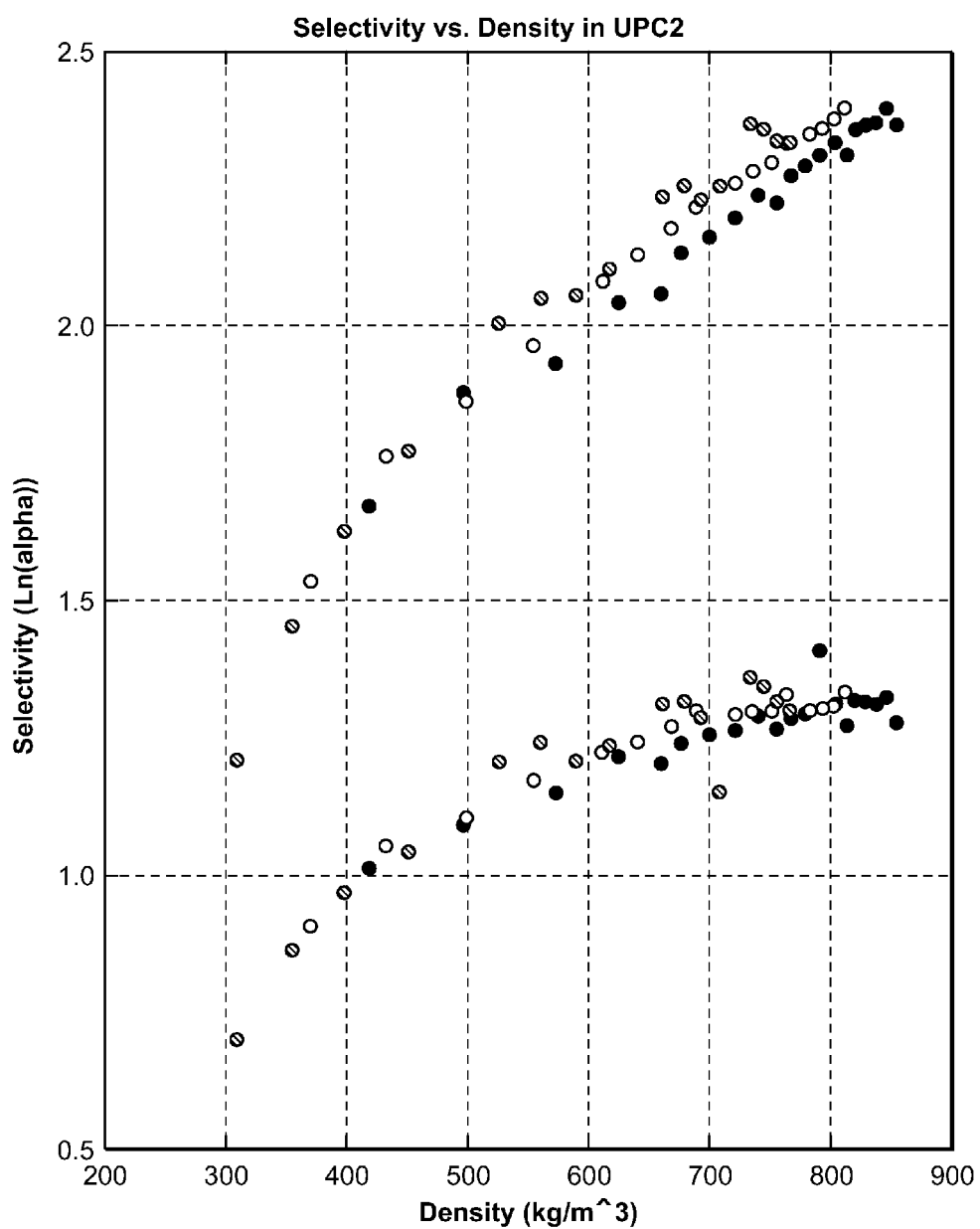
Figure 16B:
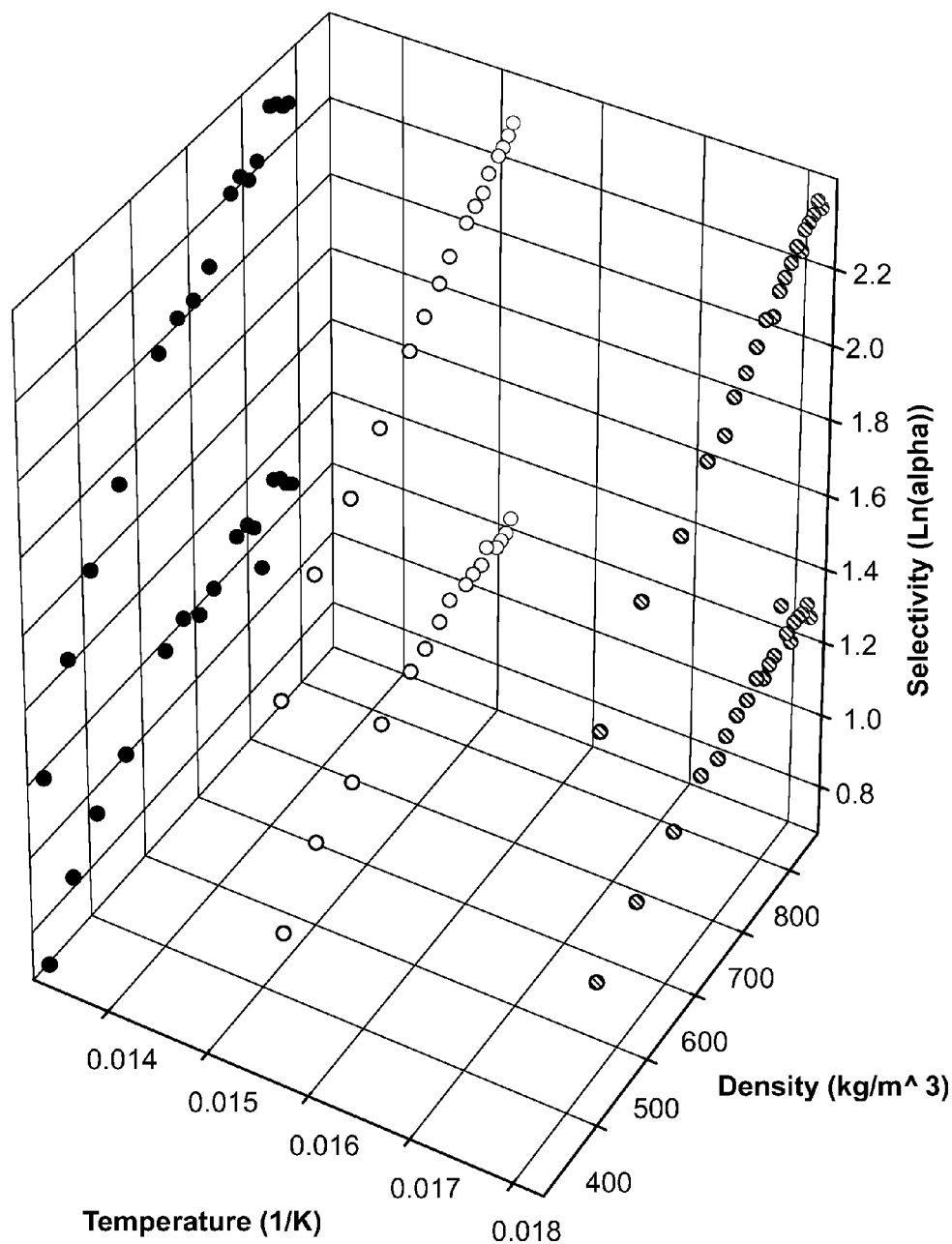

A sample mixture containing flavone, caffeine and thymine was separated on an analytical scale carbon dioxide based chromatography instrument (ACQUITY® UPC$^2$, available at Waters Technologies Corporation (Milford, Mass.)) using a BEH 2-EP® column (3.0×50 mm, 1.7 µm particle size), available at Waters Technologies Corporation (Milford, Mass.). The separation used a carbon dioxide mobile phase with 5% methanol modifier and performed at a 4 different flow rates, 4 different pressures and 3 different temperatures. A total of 48 different conditions were used. The density of the mobile phase was determined for each set of conditions. The separations were used to map the retention behavior of the analytes. FIGS. 15 and 16 show the effect on retention time (FIG. 15) and selectivity (FIG. 16) of changing density for a number of analytes.

These test results suggest that temperature has no effect independent of its effect on density. Thus, a controller can be used to affect both temperature and pressure to achieve a specific density.

Example 13

The method and apparatus of the present disclosure is used to control the average mobile phase pressure during the course of a separation. The experiment includes an analytical scale carbon dioxide based chromatography instrument (i.e., ACQUITY® UPC$^2$, available at Waters Technologies Corporation (Milford, Mass.)) equipped with a BEH 2-EP® column (3.0×50 mm, 1.7 µm particle size), available at Waters Technologies Corporation (Milford, Mass.). The system also includes at least two pressure sensors and a controller with a set of instructions as shown in FIG. 1A or 1B. A separation of a mixture of analytes, e.g., a sample mixture containing caffeine (1), carbamazepine (2), uracil (3), hydrocortisone (4), prednisolone (5) and sulfanilamide (6) is performed. An average column pressure is determined for an optimized separation of this mixture under a first set of conditions/first system (i.e., a pre-determined column pressure). A subsequent separation under a second set of conditions/second system is performed wherein the average column pressure is adjusted (iteratively or dynamically) to achieve the pre-determined average column pressure. This is a first approximation to reproduce the quality of the first optimized separation. Further optimization efforts are easier or the efforts reduced.

The average column pressure is achieved prior to sample injection. After sample injection and as the subsequent separation under a second set of conditions/second system proceeds the average column pressure may change. The average column pressure may change for a number of reasons, such as a temperature gradient being present, a decrease in carbon dioxide pressure from a carbon dioxide source (i.e., tank may be running low), or the mobile phase experiences a non-linear response to the second set of conditions. The method and apparatus of the present disclosure is used to adjust the average column pressure during the second separation to return to, or maintain the pre-determined column pressure. The adjustment is done to the ABPR and at intervals that may be less than about 1 sec. The average column pressure during the second separation is held to within about 5% of the pre-determined average pressure throughout the second separation.

What is claimed is:

1. A method of controlling mobile phase density or pressure in a carbon dioxide based separation system, comprising:

measuring a first mobile phase density or pressure at a first sensor located upstream of a chromatography column, and a second mobile phase density or pressure at a second sensor located downstream of the chromatography column to generate a first set of measurements;

calculating an average mobile phase density or pressure in the system from the first set of measurements using a controller in communication with the first and second sensors;

comparing the average mobile phase density or pressure with a pre-determined average mobile phase density or pressure; and adjusting at least one system component or parameter to achieve the pre-determined average mobile phase density or pressure.

2. The method of claim 1, further comprising
transmitting the first set of measurements to the controller to calculate the average mobile phase density or pressure in the system.

3. The method of claim 1, wherein the first mobile phase density or pressure and the second mobile phase density or pressure are measured simultaneously.

4. The method of claim 1, wherein the at least one system component or parameter adjusted is a back pressure regulator.

5. The method of claim 4, wherein the back pressure regulator is adjusted to a produce a higher pressure in the system if the average mobile phase density or pressure value is lower than the pre-determined average mobile phase density or pressure, and wherein the back pressure regulator is adjusted to produce a lower pressure in the system if the average mobile phase density or pressure value is higher than the pre-determined average mobile phase density or pressure.

6. The method of claim 1, wherein the mobile phase density or pressure in the system is at equilibrium when the at least one system component or parameter is adjusted.

7. The method of claim 1, wherein the mobile phase density or pressure in the system is not at equilibrium when the at least one system component or parameter is adjusted.

8. The method of claim 1, further comprising repeating the determining, comparing and adjusting steps until the pre-determined average mobile phase density or pressure is achieved.

9. The method of claim 8, wherein the time between consecutive adjustments of the at least one system component or parameter is less than about 10 seconds.

10. The method of claim 1, wherein the first sensor is a first pressure sensor capable of measuring a first mobile phase pressure in the system and the second sensor is a second pressure sensor capable of measuring a second mobile phase pressure in the system.

11. The method of claim 10, wherein the first pressure sensor is contained in or connected to a pump.

12. The method of claim 10, wherein the second pressure sensor is contained in or connected to a back pressure regulator.

13. The method of claim 12, wherein the first sensor is a first density sensor capable of measuring a first mobile phase density in the system and the second sensor is a second density sensor capable of measuring a second mobile phase density in the system.

14. The method of claim 1, wherein determining the average mobile phase density or pressure includes determining the average mobile phase density or pressure across one or more components of the carbon dioxide based separation system.

15. The method of claim 1, wherein determining the average mobile phase density or pressure includes determining the average mobile phase density or pressure across the carbon dioxide based separation system at initial gradient conditions and final gradient conditions.

16. The method of claim 1, wherein determining the average mobile phase density or pressure includes determining the average mobile phase density or pressure across the carbon dioxide based separation system over a specified time period.

17. A carbon dioxide based separation system comprising:
a pump;
a column located downstream of the pump;
at least one back pressure regulator located downstream of the column,
a first sensor located upstream of the column, wherein the first sensor is capable of measuring a first mobile phase density or pressure in the system;
a second sensor located downstream of the column, wherein the second sensor is capable of measuring a second mobile phase density or pressure in the system;
a controller in signal communication with the first and second sensors; and
a set of instructions utilized by the controller, wherein the controller is capable of averaging the first and the second mobile phase density or pressure measurements to determine an average mobile phase density or pressure value and adjusting at least one system component or parameter to achieve a pre-determined average mobile phase density or pressure in the system in response to the average mobile phase density or pressure value;
the carbon dioxide based separation system being configured to perform the method of claim 1.

* * * * *